(12) United States Patent
Sharma et al.

(10) Patent No.: US 10,085,957 B2
(45) Date of Patent: Oct. 2, 2018

(54) BENZOIC ACID COMPOUNDS FOR REDUCING URIC ACID

(71) Applicant: Wellstat Therapeutics Corporation, Gaithersburg, MD (US)

(72) Inventors: Shalini Sharma, Gaithersburg, MD (US); Reid W. Von Borstel, Potomac, MD (US)

(73) Assignee: Wellstat Therapeutics Corporation, Rockville, MD (US)

( * ) Notice: Subject to any disclaimer, the term of this patent is extended or adjusted under 35 U.S.C. 154(b) by 0 days.

(21) Appl. No.: 15/293,365

(22) Filed: Oct. 14, 2016

(65) Prior Publication Data

US 2017/0042844 A1    Feb. 16, 2017

Related U.S. Application Data

(62) Division of application No. 13/821,402, filed as application No. PCT/US2011/050475 on Sep. 6, 2011, now abandoned.

(60) Provisional application No. 61/380,882, filed on Sep. 8, 2010.

(51) Int. Cl.
| | |
|---|---|
| A61K 31/192 | (2006.01) |
| A61K 45/06 | (2006.01) |
| C07C 65/24 | (2006.01) |
| C07C 205/59 | (2006.01) |

(52) U.S. Cl.
CPC ........... *A61K 31/192* (2013.01); *A61K 45/06* (2013.01); *C07C 65/24* (2013.01); *C07C 205/59* (2013.01)

(58) Field of Classification Search
None
See application file for complete search history.

(56) References Cited

U.S. PATENT DOCUMENTS

| | | |
|---|---|---|
| 4,098,816 A | 7/1978 | Thorne et al. |
| 4,820,794 A | 4/1989 | Darnell et al. |
| 5,219,477 A | 6/1993 | Nader et al. |
| 6,677,473 B1 | 1/2004 | Madison et al. |
| 7,547,802 B2 | 6/2009 | Sharma |
| 7,605,181 B2 | 10/2009 | Hodge et al. |
| 7,615,575 B2 | 11/2009 | Hodge et al. |
| 7,932,290 B2 | 4/2011 | Hodge et al. |
| 7,947,735 B2 | 5/2011 | Sharma et al. |
| 8,178,675 B2 | 5/2012 | Romantsev et al. |
| 8,338,480 B2 | 12/2012 | von Borstel et al. |
| 8,410,154 B2 | 4/2013 | O'Neil et al. |
| 8,546,448 B2 | 10/2013 | Sharma et al. |
| 8,829,058 B2 | 9/2014 | O'Neil et al. |
| 8,889,724 B2 | 11/2014 | O'Neil et al. |
| 9,115,072 B2 | 8/2015 | O'Neil et al. |
| 2002/0019360 A1* | 2/2002 | Kivlighn ............. A61K 31/195 514/44 R |

(Continued)

FOREIGN PATENT DOCUMENTS

| | | |
|---|---|---|
| JP | 10120625 A | 5/1998 |
| WO | 1996025383 A1 | 8/1996 |
| WO | 2004073611 A2 | 9/2004 |
| WO | 2009134995 A2 | 11/2009 |
| WO | 2009151695 A1 | 12/2009 |
| WO | 2011046800 A1 | 4/2011 |

OTHER PUBLICATIONS

Gustafsson et al. (BMC Nephrology, 2013, vol. 14, pp. 164-172.*

(Continued)

*Primary Examiner* — Umamaheswari Ramachandran
(74) *Attorney, Agent, or Firm* — Lewis J. Kreisler

(57) ABSTRACT

Uric acid in mammalian subjects is reduced and excretion of uric acid is increased by administering a compound of Formula I. The uric acid-lowering effects of the compounds of this invention are used to treat or prevent a variety of conditions including gout, hyperuricemia, elevated levels of uric acid that do not meet the levels customarily justifying a diagnosis of hyperuricemia, renal dysfunction, kidney stones, cardiovascular disease, risk for developing cardiovascular disease, tumor-lysis syndrome, cognitive impairment, early-onset essential hypertension, and *Plasmodium falciparum*-induced inflammation.

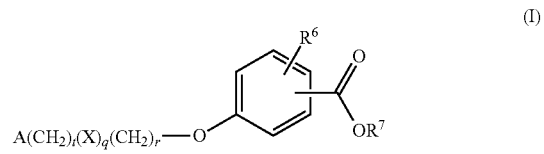

(I)

In Formula I, t is 0 or 1; q is 0 or 1; and r is 0, 1 or 2. $R^7$ is hydrogen or alkyl having from 1 to 3 carbon atoms. $R^6$ is hydrogen, hydroxy, halo, alkyl having from 1 to 3 carbon atoms, alkoxy having from 1 to 3 carbon atoms, nitro, thio, alkylthio, or cyano. X is C(O) or $NH(R^8)$ wherein $R^8$ is hydrogen or alkyl having from 1 to 3 carbon atoms; provided that when X is C(O), r is 0 and t is 0. A is phenyl, unsubstituted or substituted by 1 or 2 groups selected from halo, hydroxy, methyl, ethyl, perfluoromethyl, methoxy, ethoxy, perfluoromethoxy, nitro, and amino; or a 5 or 6 membered heteroaromatic ring having 1 or 2 ring heteroatoms selected from N, S and O and the heteroaromatic ring is covalently bound to the remainder of the compound of Formula I by a ring carbon; or cycloalkyl having from 3 to 6 ring carbon atoms wherein the cycloalkyl is unsubstituted or one or two ring carbons are independently monosubstituted by methyl or ethyl.

10 Claims, No Drawings

(56) References Cited

U.S. PATENT DOCUMENTS

2003/0149110 A1    8/2003   Hu et al.
2009/0186091 A1*   7/2009   Darlington, Jr. ....... A61K 31/19
                                                                                                            424/489
2010/0160351 A1    6/2010   Jenkins et al.

OTHER PUBLICATIONS

Patani (Chem Rev. 1996, 96, 3147-3176).*
Cirillo, et al., "Uric acid, the metabolic syndrome, and renal disease", J. Am. Soc. Nephrol. 17: S165-S168, 2006.
Baggaley, et al., "Hypolipidemic analogues of ethyl 4-benzyloxybenzoate", J. Med. Chem. 20(11): 1388-1393, 1977.
Hawley's Condensed Chemical Dictionary, 14th ed., revised by Richard J. Lewis, p. 578 (Wiley: New York, 2001).
Dorwald, "Side Reactions in Organic Synthesis: A Guide to Successful Synthesis Design" 2005 Wiley—VCH Verlag GmbH & Co.
NDA 207988 Approval. Dec. 22, 2015.
Howard, "Substitution of the N-cyanoamide function for the carboxyl group of a carboxypeptidase a substrate", Enzymologia. 36: 220-226, 1969.
Thornber, "Isosterism and molecular modification in drug design", Chem. Soc. Rev. 8: 563-580, 1979.
Maccari et al., "Identification of nnew non-carboxylic acid containing inhibitors of aldose reductase", Bioorg. Med. Chem. 18: 4049-4055, Jun. 2010.
Meanwell, "Synopsis of some recent tactical application of bioisosteres in drug design", J. Med. Chem. 54: 2529-2591, 2011.
Lasallas et al., "Structure property relationships of carboxylic acid isosteres", J. Med. Chem. 59: 3183-3203, 2016.
Ballatore et al., "Carboxylic acid (bio)isosteres in drug design", Chem. Med. Chem. 8: 385-395, 2013.
Ballatore et al., "Evaluation of the cyclopentane-1,2-dione as a potential bio-isostere of the carboxylic acid functional group", Bioorg. Med. Chem. Lett. 24: 4171-4175, 2014.
Hawley's Condensed Chemical Dictionary, pp. 822-823 (R.J. Lewis ed., 14th ed., Wiley 2001).

* cited by examiner

BENZOIC ACID COMPOUNDS FOR REDUCING URIC ACID

BACKGROUND OF THE INVENTION

Diseases caused by elevated levels of uric acid fall into two major categories: disorders caused by precipitation of uric acid crystals and diseases related to pathological effects of soluble uric acid. Gouty arthritis is the classic example of the former. Deposition of urate crystals in the kidney is also a common cause of renal dysfunction. Elevated levels of soluble uric acid are associated with a variety of disorders, including cardiovascular and renal diseases.

Gout is most commonly manifested as inflammation of one or more of the joints in the body resulting in mild to severe pain. These events may be episodic and/or chronic. Over time gout can result in the destruction of cartilage and bone, development of uric acid crystal deposits, kidney pain and dysfunction as well as kidney stones. Gout can affect other organs as well.

Gout is caused by hyperuricemia and the consequent formation and deposition of uric acid crystals in tissues, joints, kidneys and other organs. The uric acid comes from normal cell metabolism and from some types of foods and beverages. The excessive levels of uric acid are the result of too much uric acid production, impaired clearance by the kidneys (or a combination of excess production and impaired clearance), and also by some forms of medications taken for other health conditions. (Examples include diuretics, pyrazinamide, cyclosporine, low-dose aspirin, nicotinic acid and levodopa.). Many types of health conditions can also contribute to hyperuricemia and gout, including alcoholism, leukemia, lymphoma, lung cancer, tumor-lysis syndrome, smoking, psoriasis, obesity, kidney dysfunction, congestive heart failure, starvation, anemia, high blood pressure, diabetes, immobility, Lesch-Nyhan Syndrome, Down syndrome, and thyroid and parathyroid dysfunctions.

Gout is generally divided into four categories based upon progressively more severe symptoms:
1) Asymptomatic. Elevated uric acid levels in the blood, but no overt symptoms.
2) Acute gouty arthritis: Sudden onset of symptoms, often in a single joint (commonly a big toe), and then involving other joints. Symptoms include pain, swelling, redness and fever.
3) Intercritical gout: Asymptomatic phases between gout attacks.
4) Chronic tophaceous gout: A chronic condition that may include frequent attacks, constant mild pain and inflammation of joints, destruction of cartilage and bone, development of uric acid crystal deposits, kidney dysfunction and kidney stones.

Medications currently used to treat the acute symptoms of gout include nonsteroidal antiinflammatory drugs, colchicine and corticosteroids. All of these medications can produce mild to severe side effects. Other treatments for these acute symptoms are being studied, including antibodies and antagonists to inflammatory cytokines such as Interleukin 1.

Other types of medication are used in order to try to reduce the incidence or severity of future attacks by reducing levels of uric acid. The three principal classes of medication are xanthine oxidase inhibitors (for example, allopurinol), which reduce production of uric acid from xanthine; uricosuric agents (for example, sulfinpyrazone, probenecid, benzbromarone and losartan), which are intended to improve excretion of uric acid by inhibiting reuptake of secreted uric acid in the renal tubules via inhibition of uric acid transporter 1 (URAT1) (See also US Patent Application Publication No. 2007/0010670, published Jan. 11, 2007 (Japan Tobacco Inc.)) or other elements of uric acid reuptake; and uricases, for example a pegylated-uricase such as PURICASE (Savient's pegylated recombinant mammalian uricase). These medications also often result in significant and undesirable side effects. For example, allopurinol has been reported to cause at least 100 cases of Stevens-Johnson/Toxic Epidermal Necrolysis and approximately 30 deaths each year in Europe (Halevy et al., Allopurinol is the most common cause of Stevens-Johnson syndrome and toxic epidermal necrolysis in Europe and Israel. J Am Acad Dermatol. 58(1):25-32, 2008). Probenicid and benzbromarone have been taken off the market in a number of countries due to undesirable side effects, such as liver failure in the case of benzbromarone. Patient compliance in taking these drugs is reportedly very poor (A. A. Reidel et al. "Compliance with Allopurinol Therapy among Managed Care Enrollees with Gout: A Retrospective Analysis of Administrative Claims." Journal of Rheumatology 2004; 31:1575-1581), presumably because of the side effects and/or lack of benefit.

More than 5 million people in the U.S. have gout (National Health and Nutrition Examination Survey 111, 1988-1994). The prevalence of hyperuricemia and gout in the U.S. in 1999 was reported to be 41 per 1,000 and 14 per 1,000 in the U.K. (T. R. Mikuls et al., "Gout Epidemiology: Results for the UK General Practice Research Database, 1990-1999." Annals of the Rheumatic Diseases 2005; 64:267-272). Subsequent reports indicate that the prevalence in the U.S., U.K. and other countries has been climbing steadily. (K. L. Wallace et al., "Increasing Prevalence of Gout and Hyperuricemia over 10 Years Among Older Adults in a Managed Care Population." Journal of Rheumatology 2004; 31: 1582-1587). More recent data suggest that far more than 5 million Americans now have diagnosable gout. (E. Krishnan et al., "Gout in Ambulatory Care Settings in the United States." Journal of Rheumatology 2008; 35(3): 498-501).

Hyperuricemia and gout are particularly significant issues in organ transplant recipients (Stamp, L., et al, "Gout in solid organ transplantation: a challenging clinical problem", Drugs (2005) 65(18): 2593-2611). Uric acid is often elevated in patients with renal transplants, and common immunosupressive drugs such as cyclosporine can cause particularly severe hyperuricemia. In transplant patients, allopurinol is contra-indicated due to interactions with some immunosupressants such as azathioprine, and due to bone marrow failure caused by the combination. Furthermore, elevated uric acid may contribute to graft failure (Armstrong, K. A. et al., "Does Uric Acid Have a Pathogenetic Role in Graft Dysfunction and Hypertension in Renal Transplant Patients?" Transplantation (2005) 80(11): 1565-1571). Therefore, there is a particularly acute need for safe agents that reduce hyperuricemia in transplant recipients.

Diseases related to elevated soluble uric acid often involve vascular problems: hypertension (Sundstrom et al., Relations of serum uric acid to longitudinal blood pressure tracking and hypertension incidence. Hypertension. 45(1): 28-33, 2005), prehypertension (Syamela, S. et al., Association between serum uric acid and prehypertension among US adults. J Hypertens. 25 (8) 1583-1589, (2007), atherosclerosis (Ishizaka et al., Association between serum uric acid, metabolic syndrome, and carotid atherosclerosis in Japanese individuals. Arterioscler Thromb Vasc Biol. (5): 1038-44, 2005), peripheral artery disease (Shankar, A. et al., Association between serum uric acid level and peripheral artery disease. Atherosclerosis doi 10: 1016, 2007), vascular inflammation (Zoccali et al., Uric acid and endothelial dysfunction in essential hypertension. J Am Soc Nephrol. 17(5):1466-71, 2006), heart failure (Strasak, A. M. et al., Serum uric acid and risk of cardiovascular mortality: A prospective, long-term study of 83,683 Austrian men, Clin Chem. 54 (2) 273-284, 2008; Pascual-Figal, Hyperuricaemia and long-term outcome after hospital discharge in acute heart failure patients. Eur J Heart Fail. 2006 Oct. 23; [Epub ahead of print]; Cengel, A., et al., "Serum uric Acid Levels as a Predictor of In-hospital Death in Patients Hospitalized for Decompensated Heart Failure." Acta Cardiol. (October 2005) 60(5): 489-492), myocardial infarctions (Strasak, A. M. et al.; Bos et al., Uric acid is a risk factor for myocardial infarction and stroke: the Rotterdam study. Stroke. 2006 June; 37(6):1503-7), renal dysfunction (Cirillo et al., Uric Acid, the metabolic syndrome, and renal disease. J Am Soc Nephrol. 17(12 Suppl 3):S165-8, 2006; Z. Avram and E. Krishnan, Hyperuricemia—where nephrology meets rheumatology. Rheumatology (Oxford), 47(7): 960-964, 2008), and strokes (Bos et al., 2006). Uric acid directly causes endothelial dysfunction (Kanellis, et al., Uric acid as a mediator of endothelial dysfunction, inflammation, and vascular disease. Semin Nephrol. 25(1):39-42, 2005; Khosla et al, Hyperuricemia induces endothelial dysfunction. Kidney Int. 67(5):1739-42, 2005). In children and adolescents, early-onset essential hypertension is associated with elevated serum uric acid, and reduction of uric acid with allopurinol reduces blood pressure in these patients (Feig and Johnson, The role of uric acid in pediatric hypertension. J Ren Nutrition 17(1): 79-83, 2007; D. I. Feig et al., Effect of allopurinol on blood pressure of adolescents with newly diagnosed essential hypertension. JAMA 300(8): 924-932, 2008. Feig et al. also state that this is a new therapeutic approach but that the side effects of existing drugs to lower uric acid may limit or prevent their use. Hyperuricemia is an independent risk factor in all of these conditions.

Elevated soluble uric acid is also associated with or directly induces inflammatory responses. For example, uric acid is transported into vascular smooth muscle cells via organic acid transporters, especially the urate transporter URAT1, and then stimulates vascular smooth muscle cells to produce C-reactive protein, MCP-1 and other cytokines, thereby stimulating proliferation and other changes associated with atherosclerosis (Price et al., Human vascular smooth muscle cells express a urate transporter. J Am Soc Nephrol. 17(7):1791-5, 2006; Kang et al., Uric acid causes vascular smooth muscle cell proliferation by entering cells via a functional urate transporter. Am J Nephrol. 2005 25(5):425-33 (2005); Yamamoto et al., Allopurinol reduces neointimal hyperplasia in the carotid artery ligation model in spontaneously hypertensive rats. Hypertens. Res. 29 (11) 915-921, 2006), stimulates human mononuclear cells to produce IL-1β, IL-6 and TNF-α, causes marked increases in TNF-α when infused into mice, activates endothelial cells and platelets, and increases platelet adhesiveness (Coutinho et al., "Associations of Serum Uric Acid with Markers of Inflammation, Metabolic Syndrome, and Subclinical Coronary Atherosclerosis", Amer. J. Hypertens. (2007) 20: 83-89; Levya, F., et al., "Uric Acid in Chronic Heart Failure: A Marker of Chronic Inflammation", Eur. Heart J. (1998) 19(12): 1814-1822.). Uric acid has also been shown to inhibit bioavailability of endothelial nitric oxide and activate the renin-angiotensin system. (T. S. Perlstein et al., Uric acid and the state of the intrarenal renin-angiotensin system in humans. Kidney International. 66:1465-1470, 2004). Inokuchi et al. have shown that Interleukin 18 (IL-18) and other inflammatory agents reflect local inflammation associated with gout and that urate crystals accelerate activation of IL-18 (T. Inokuchi et al., Plasma IL-18 and other inflammatory cytokines in patients with gouty arthritis and monosodium urate monohydrate crystal-induced secretion of IL-18. Cytokine. 33(1): 21-27, 206), which appears to have a causative role in renal failure. IL-18 and other cytokines are also significantly elevated in people who do not have gout per se but who merely have elevated uric acid levels (C. Ruggiero et al. Uric acid and inflammatory markers. (C. Ruggiero et al., Uric acid and inflammatory markers. European Heart Journal. 27: 1174-1181, 2006).

Hyperuricemia is also associated with cognitive impairment and other forms of central nervous system dysfunction. (Schretlen, D. J. et al., "Serum Uric Acid and Cognitive Function in Community-Dwelling Older Adults", Neuropsychology (January 2007) 21(1): 136-140; Watanabe, S., et al., "Cerebral Oxidative Stress and Mitochondrial Dysfunction in Oxonate-Induced Hyperuricemic Mice", J. Health Science (2006) 52: 730-737).

Elevated serum uric acid levels are also associated with increased risk of cancer and cancer mortality. (Strasak, A M et al. (2007) Serum uric acid and risk of cancer mortality in a large prospective male cohort. Cancer Causes Control 18 (9) 1021-1029; Strasak, A M et al. (2007) The role of serum uric acid as an antioxidant protecting against cancer: prospective study in more than 28,000 older Austrian women. Annals Oncol 18 (11) 1893-1897; Jee, S A et al. (2004) Serum uric acid and risk of death from cancer, cardiovascular disease or all causes in men Eur. J. Cardiovascular Prev. Rehab. 11 (3) 185-191)

Elevated levels of uric acid are associated with prediabetes, insulin resistance, the development of Type 2 diabetes, and an increased probability of a variety of undesirable conditions in people with diabetes, such as peripheral artery disease, strokes, and increased mortality risk, (Ioachimescu, A. G. et al. (2007) Serum uric acid, mortality and glucose control in patients with Type 2 diabetes mellitus: a PreCIS database study Diabet. Med. 24 (12) 1369-1374; Perry, I. J. et al (1995) Prospective study of risk factors for development of non-insulin dependent diabetes in middle aged British men BMJ 310 (6979) 560-564; Chien, K-L et al. (2008) Plasma uric acid and the risk of Type 2 diabetes in a Chinese community Clin. Chem. 54 (2) 310-316; Sautin, Y. Y. et al. (2007) Adverse effects of the classic antioxidant uric acid in adipocytes: NADPH oxidase-mediated oxidative/nitrosative stress Am. J. Physiol. Cell Physiol. 293: C584-0596; Tseng, C. H. (2004) Independent association of uric acid levels with peripheral artery disease in Taiwanese patients with Type 2 diabetes Diabet. Med. 21 (7) 724-729; Lehto, S. et al. (1998) Serum uric acid is a strong predictor of stroke in patients with non-insulin dependent diabetes mellitus Stroke 29: 635-639.)

Elevated levels of uric acid are a defining feature of Lesch-Nyhan Syndrome. People with sleep apnea or sleep-disordered breathing also have elevated of uric acid (Saito, H. et al., Tissue hypoxia in sleep apnea syndrome assessed by uric acid and adenosine. Chest 122: 1686-1694, 2002; Verhulst, S. L., et al., Sleep-disordered breathing and uric acid in overweight and obese children and adolescents. Chest 132: 76-80, 2007)

Elevated uric acid is associated with preeclampsia (Bainbridge, S. A. and Roberts, J. M., Uric acid as a pathogenic factor in preeclampsia. Placenta Dec. 17, 2007 epub ahead of print).

"Uric acid is a major contributor of the inflammatory response triggered by *P. falciparum* in human peripheral blood mononuclear cells . . . . [T]he inflammatory reaction induced by *P. falciparum* is considered a major cause of malaria pathogenesis . . . ." PLoS ONE 2009; 4(4):e5194. Epub 2009 Apr. 17.

There is a significant medical need for new medications that can safely, conveniently and effectively treat and prevent disorders related to elevation of blood uric acid, whether such diseases are due to crystallization of uric acid or to effects of supranormal (whether by an individual or a population-based standard) levels of soluble uric acid.

SUMMARY OF THE INVENTION

This invention provides a compound represented by Formula I.

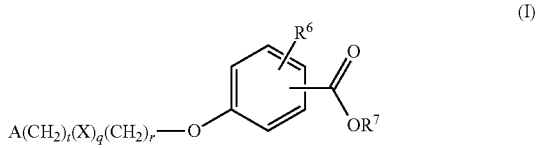

(I)

In Formula I, t is 0 or 1; q is 0 or 1; and r is 0, 1 or 2. $R^7$ is hydrogen or alkyl having from 1 to 3 carbon atoms. $R^6$ is hydrogen, hydroxy, halo, alkyl having from 1 to 3 carbon atoms, alkoxy having from 1 to 3 carbon atoms, nitro, thio, alkylthio, or cyano. X is C(O) or NH($R^8$) wherein $R^8$ is hydrogen or alkyl having from 1 to 3 carbon atoms; provided that when X is C(O), r is 0 and t is 0. A is phenyl, unsubstituted or substituted by 1 or 2 groups selected from halo, hydroxy, methyl, ethyl, perfluoromethyl, methoxy, ethoxy, perfluoromethoxy, nitro, and amino; or a 5 or 6 membered heteroaromatic ring having 1 or 2 ring heteroatoms selected from N, S and O and the heteroaromatic ring is covalently bound to the remainder of the compound of Formula I by a ring carbon; or cycloalkyl having from 3 to 6 ring carbon atoms wherein the cycloalkyl is unsubstituted or one or two ring carbons are independently monosubstituted by methyl or ethyl. Esters and other prodrugs of compounds of Formula I are also included in this invention.

This invention provides a method of reducing the uric acid concentration in blood of, or increasing uric acid excretion from, a mammalian subject, comprising administering to the subject a compound of this invention in an amount effective to reduce the uric acid concentration in blood of, or increase uric acid excretion from, the subject. This invention provides a compound of this invention for use in reducing the uric acid concentration in blood of, or increasing uric acid excretion from, a mammal. This invention provides the use of a compound of this invention in the manufacture of a medicament for reducing the uric acid concentration in blood of, or increasing uric acid excretion from, a mammal. This invention provides a pharmaceutical composition for use in reducing the uric acid concentration in blood of, or increasing uric acid excretion from, a mammalian subject comprising a compound of this invention in an amount effective to reduce the uric acid concentration in blood of, or increase uric acid excretion from, the subject. This invention provides a kit comprising one or more unit oral doses of a compound of this invention, and instructions for administering the compound to reduce the uric acid concentration in blood of, or increasing uric acid excretion from, a mammalian subject.

Reducing uric acid as described herein can be used to treat or prevent a variety of conditions including gout (any or all of: asymptomatic gout, acute gouty arthritis, intercritical gout, and chronic tophaceous gout), hyperuricemia, elevated levels of uric acid that do not meet the levels customarily justifying a diagnosis of hyperuricemia, renal dysfunction, kidney stones, cardiovascular disease, risk for developing cardiovascular disease and other consequences of hyperuricemia, cognitive impairment, early-onset essential hypertension, and *Plasmodium falciparum*-induced inflammation.

This invention is based on the observation that compounds of this invention inhibited URAT1 in vitro, as shown in Example 6. Inhibition of URAT1 is an established in vitro model for lowering uric acid in vivo.

DETAILED DESCRIPTION OF THE INVENTION

Definitions

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and an alkyl having four carbon atoms can be n-butyl, 1-methylpropyl, 2-methylpropyl or t-butyl.

As used herein the term "halo" refers to one or more of fluoro, chloro, bromo and iodo. As used herein the term "perfluoro" as in perfluoromethyl or perfluoromethoxy, means that the group in question has fluorine atoms in place of all of the hydrogen atoms.

Certain chemical Compounds are referred to herein by their chemical name or by the two-letter code shown below. Compounds FA through FD are included within the scope of Formula I shown above.

FA 3-(2,6-dimethylbenzyloxy)-4-methylbenzoic acid
FB 3-(2,6-dimethylbenzyloxy)-4-nitrobenzoic acid
FC 3-(2,6-dimethylbenzyloxy)-4-methoxybenzoic acid
FD 3-(2,6-dimethylbenzyloxy)-4-fluorobenzoic acid
FE 4-amino-3-(2,6-dimethylbenzyloxy)benzoic acid
EH 2-(3-(2,6-Dimethylbenzyloxy)-4-methylphenyl)acetic acid As used herein the transitional term "comprising" is open-ended. A claim utilizing this term can contain elements in addition to those recited in such claim.

As used in the claims the word "or" means "and/or" unless such reading does not make sense in context. So for example the phrase "reducing the uric acid concentration in blood of or increasing uric acid excretion from, a mammalian subject" is equivalent to "reducing the uric acid concentration in blood of and/or increasing uric acid excretion from, a mammalian subject.

Compounds of the Invention

In an embodiment of the compound of this invention, the compound is in substantially (at least 98%) pure form.

In an embodiment of the invention described in the Summary above, A is substituted (as defined above) or unsubstituted phenyl, for example 2,6-dimethylphenyl. In other embodiments r is 1, t is 0, and q is 0. In another embodiment $R^6$ is methyl, nitro, methoxy, or fluoro.

The substituents around the central phenyl ring can be located in the ortho, meta or para position with respect to one another. Preferably the bulky substituent (i.e. other than $R^6$ and the carboxylic acid/ester moieties) around the central phenyl ring is in the 3-position (i.e. meta) with respect to the carboxylic acid/ester moiety. When the bulky substituent is in the 3-position with respect to the carboxylic acid/ester moiety, $R^6$ is in the 4-position (i.e. para) with respect to the carboxylic acid/ester moiety.

In an embodiment of Formula I, A is substituted (as defined above) or unsubstituted phenyl, t is 0, q is 0, and r is 1. In a more specific embodiment A is 2,6-dimethylphenyl. In another more specific embodiment $R^6$ is methyl, nitro, methoxy, or fluoro.

In an embodiment of this invention the Compound is represented by Formula IA. Preferably $R^6$ is in the 4-position (i.e. para) with respect to the carboxylic acid/ester moiety.

In a more specific embodiment the Compound is represented by Formula IA1. In a still more specific embodiment the Compound is represented by Formula IA1a. In Formula IA the variables are as defined above. In Formulas IA1 and IA1a two of $R^1$, $R^2$, $R^3$, $R^4$ and $R^5$ are selected from the group consisting of hydrogen, halo, hydroxy, methyl, ethyl, perfluoromethyl, methoxy, ethoxy and perfluoromethoxy, the remainder are hydrogen; and the other variables are as defined above. In more specific embodiments A is 2,6-dimethylphenyl, i.e. $R^1$ is methyl and $R^5$ is methyl. In other embodiments of Formulas IA, IA1 and IA1a, $R^6$ is methyl, nitro, methoxy, or fluoro. Nonlimiting examples of compounds of Formula I include Compounds FA, FB, FC, and FD.

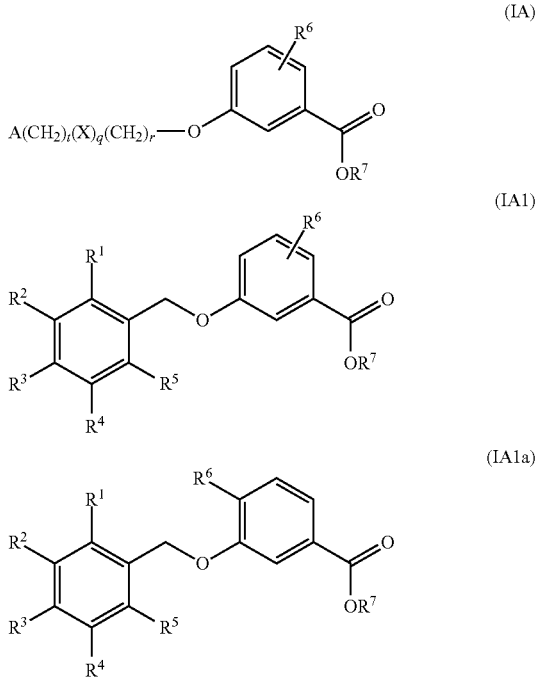

The compounds of Formula I can be made in accordance with the reaction schemes below.

Reaction Schemes

The compound of formula I where t is 0 or 1, r is 0, 1 or 2, and q is 0 or 1, $R^6$ is hydrogen, hydroxy, halo, alkoxy having from 1 to 3 carbon atoms, alkyl having from 1 to 3 carbon atoms, nitro, thio, alkylthio or cyano, $R^7$ is hydrogen or alkyl having from 1 to 3 carbon atoms, when X is C(O), r is 0 and t is 0 or X is NH($R^8$) wherein $R^8$ is hydrogen or alkyl having from 1 to 3 carbon atoms, i.e. compounds of formula:

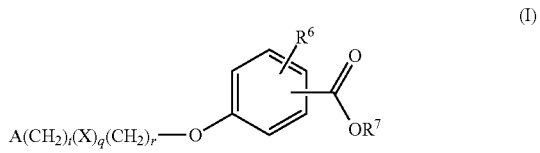

wherein A is described as above, can be prepared via reaction scheme of Scheme 1.

In the reaction scheme of Scheme 1, A, X, q, t, r, $R^6$, $R^7$, and $R^8$ are described as above. $R^9$ is alkyl group having from 1 to 3 carbon atoms or benzyl group and Y is a halide. The compound of formula II can be converted to the compound of formula III by esterification of compound of formula II with methanol, ethanol or propanol. The reaction can be carried out either by using catalyst for example $H_2SO_4$, TsOH and the like or by using dehydrating agent for example DCC/DMAP and the like. Any of the conditions conventional in such esterification reactions can be utilized to carry out the reaction of step (a).

In the case where X is C(O), the compound of formula II can be reacted with the benzyl bromide in the presence of base for example, pyridine, triethylamine, potassium carbonate, cesium carbonate and the like. The reaction can be carried out at temperatures from 25° C.-100° C. for 6 to 72 hours in the solvent for example, dimethylformamide, dimethyl sulfoxide, dichloromethane, tetrahydrofuran to produce the compound of formula III. Any conditions conventional in such alkylation reactions can be utilized to carry out the reaction of step (a).

In the second step, the compound of formula (III) can be converted to the compound of formula VII via reaction of step (b) using Mitsunobu condensation with IV utilizing triphenylphosphine and diethyl azodicarboxylate or diisopropyl azodicarboxylate. The reaction can be carried out in a suitable solvent for example tetrahydrofuran. Any of the conditions conventionally used in Mitsunobu reactions can be utilized to carry out the reaction of step (b).

In the case where X is C(O), the compound of formula III can be reacted with the compound of formula VI in the presence of dehydrating agent for example dicyclohexylcarbodiimide, alkyl chloroformate and triethylamine, DCC and an aminopyridine, triethylamine and N,N'-carbonyldiimidazole and the like. Any conditions conventional in such esterification reactions can be utilized to carry out the reaction of step (b).

The compound of formula VII can also be prepared by etherifying or alkylating the compound of formula III from step (a) with the compound of formula V via reaction of step (b). In the compound of formula V, Y, include but are not limited to mesyloxy, tosyloxy, chloro, bromo, iodo, and the like. Any conventional method of alkylating a hydroxyl group by reaction with a leaving group can be utilized to carry out the reaction of step (b).

The compound of formula VII is the compound of formula I where $R^7$ is alkyl having from 1 to 3 carbon atoms.

The compound of formula VII can be converted to the compound of formula VIII via reaction of step (c) where $R^7$ is H by ester hydrolysis. Any conventional method of ester hydrolysis will produce the compound of formula VIII where $R^7$ is H.

In the case where X is C(O), the benzyl group from the compound of formula VII can be removed by catalytic hydrogenation in the presence of transition metal catalyst for example, raney nickel, palladium-on-charcoal, platinum metal or its oxide under hydrogen atmosphere. Any of the conditions conventional in such catalytic hydrogenation can be utilized to carry out the reaction of step (c) to give the compound of formula VIII where $R^7$ is H and X is C(O).

The compound of formula VIII is the compound of formula I where $R^7$ is H.

The products in all the steps can be isolated and purified by techniques such as extraction, evaporation, chromatography, and recrystallization.

If A is phenyl substituted by hydroxy or amino group, it is generally preferred to protect those groups by utilizing suitable protecting groups, which are known in the art. The suitable protecting group can be described in the Protective Groups in Organic Synthesis by T. Greene.

The protecting group can be deprotected utilizing suitable deprotecting reagents such as those described in Protective Groups in Organic Synthesis by T. Greene.

Reaction Scheme 1

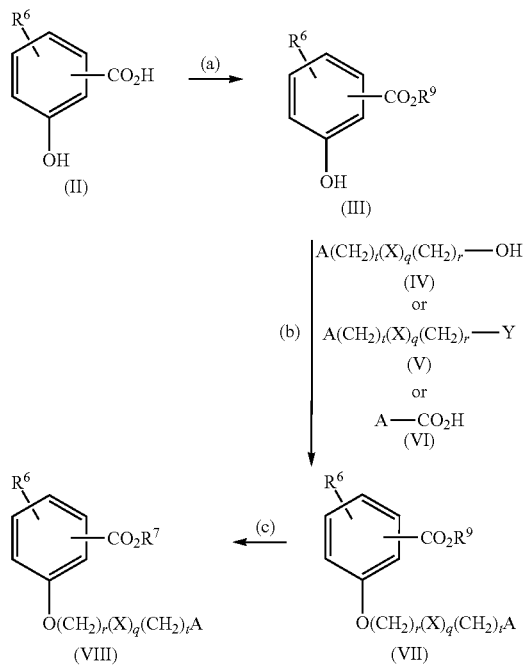

The compound of formula IV, where t is 0 or 1, r is 0, 1 or 2 and q is 0, i.e. compounds of formula:

$$A-(CH_2)_t(X)_q(CH_2)_r—OH \quad (IV)$$

and the compound of formula V, where t is 0 or 1, r is 0, 1 or 2 and q is 0, i.e. compounds of formula:

$$A-(CH_2)_t(X)_q(CH_2)_r—Y \quad (V)$$

can be prepared via reaction scheme of Scheme 2.

In the reaction scheme of Scheme 2, A is described as above. Y is halide.

The compound of formula IX can be reduced to the compound of formula X via reaction of step (d). The reaction can be carried out utilizing a conventional reducing agent for example alkali metal hydride such as lithium aluminum hydride, or borane dimethyl sulfide complex and the like. The reaction can be carried out in a suitable solvent, such as tetrahydrofuran, ether, dichloromethane and the like. Any of the conditions conventional in such reduction reactions can be utilized to carry out the reaction of step (d). The compound of formula X is the compound of formula IV where t is 0 and r is 1.

The compound of formula X can be converted to the compound of formula XI by displacing hydroxyl group with a halogen group preferred halogen being bromo or chloro. Appropriate halogenating reagents include but are not limited to thionyl chloride, oxalyl chloride, bromine, phosphorous tribromide, carbon tetrabromide and the like. Any conditions conventional in such halogenation reactions can be utilized to carry out the reaction of step (e).

The compound of formula XI is the compound of formula V where t is 0 and r is 1.

The compound of formula XI can be converted to the compound of formula XII by reacting XI with alkali metal cyanide for example sodium or potassium cyanide. The reaction is carried out in a suitable solvent, such as ethanol, dimethyl sulfoxide, dimethylformamide and the like. Any of the conditions conventionally used in the preparation of nitrile can be utilized to carry out the reaction of step (f).

The compound of formula XII can be converted to the compound of formula XIII via reaction step (g) by hydrolysis. In carrying out this reaction it is generally preferred to utilize basic hydrolysis, for example aqueous sodium hydroxide. Any of the conditions conventionally used in hydrolysis of nitrile can be utilized to carry out the reaction of step (g).

The compound of formula XIII can be reduced to give the compound of formula XIV via reaction of step (h). This reaction can be carried out in the same manner as described hereinbefore in the reaction of step (d).

The compound of formula XIV is the compound of formula IV where t is 1 and r is 1.

The compound of formula XIV can be converted to the compound of formula XV via reaction of step (i) in the same manner as described hereinbefore in connection with the reaction of step (e).

The compound of formula XV is the compound of formula V where t is 1 and r is 1.

The compound of formula XV can be converted to the compound of formula XVI via reaction of step (j) in the same manner as described hereinbefore in connection with the reaction of step (f).

The compound of formula XVI can be hydrolyzed by base in the same manner as described hereinbefore in connection with the reaction of step (g) to give the compound of formula XVII via reaction of step (k).

The compound of formula XVII can be converted to the compound of formula XVIII via reaction of step (l) in the same manner as described hereinbefore in connection with the reaction of step (d).

The compound of formula XVIII is the compound of formula IV where t is 1 and r is 2.

The compound of formula XVIII can be converted to the compound of formula XIX via reaction of step (m) in the same manner as described hereinbefore in connection with the reaction of step (e).

The compound of formula XIX is the compound of formula V where t is 1 and r is 2.

The product of the each step can be isolated and purified by techniques such as extraction, evaporation, chromatography, and recrystallization.

If A is phenyl substituted by hydroxy or amino groups, it is generally preferred to protect those groups by utilizing suitable protecting groups, which are known in the art. The suitable protecting group can be described in the Protective Groups in Organic Synthesis by T. Greene.

The protecting group can be deprotected utilizing suitable deprotecting reagents such as those described in Protective Groups in Organic Synthesis by T. Greene.

Reaction Scheme 2

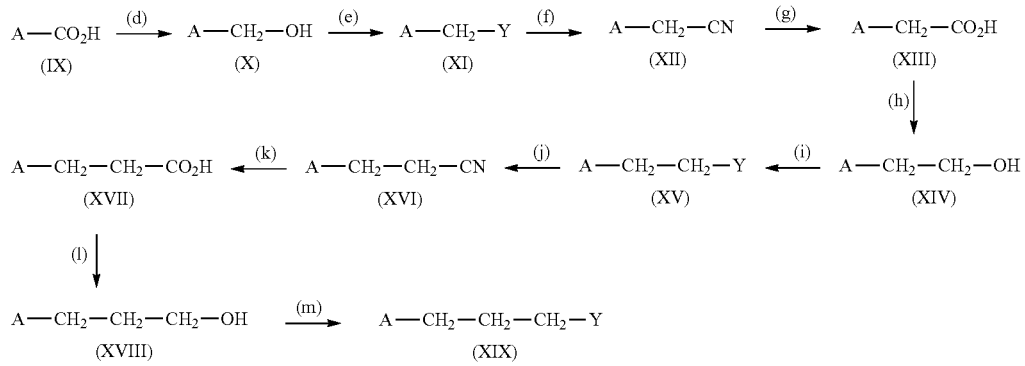

The compound of formula IV, where t is 0 or 1, r is 0, 1 or 2 and q is 1 and X is $N(R^8)$ wherein $R^8$ is hydrogen or alkyl having from 1 to 3 carbon atoms, i.e. compounds of formula:

$$A\text{-}(CH_2)_t(X)_q(CH_2)_r\text{—OH} \quad (IV)$$

and the compound of formula V, where t is 0 or 1, r is 0, 1 or 2 and q is 1 and X is $N(R^8)$ wherein $R^8$ is hydrogen or alkyl having from 1 to 3 carbon atoms, i.e. compounds of formula:

$$A\text{-}(CH_2)_t(X)_q(CH_2)_r\text{—Y} \quad (V)$$

can be prepared via reaction scheme of Scheme 3.

In the reaction scheme of Scheme 3, A, t, r and $R^8$ are described as above. Y is chloro or bromo.

The compound of formula XX can be mesylated to furnish the compound of formula XXI via the reaction of step (n). Any conventional conditions to carry out the mesylation reaction of a hydroxyl group can be utilized to carry out the step (n). The compound of formula XXI can be heated with the compound of formula XXII to produce the compound of formula XXIII. Any of the conditions conventional in producing amino alcohols can be utilized to carry out the reaction of step (o).

The compound of formula XXIII is the compound of formula IV where q is 1.

In the compound of formula XXIII, alcohol can be displaced by chloro or bromo by treating the compound of formula XXIII with thionyl chloride, bromine, phosphorus tribromide, oxalyl chloride, carbon tetrabromide and the like to produce the compound of formula XXIV. Any conventional methods to displace alcohol with chloro or bromo can be utilized to carry out the reaction of step (p).

The compound of formula XXIV is the compound of formula V where q is 1.

The product of each step can be isolated and purified by techniques such as extraction, evaporation, chromatography, and recrystallization.

If A is phenyl substituted by hydroxy or amino groups, it is generally preferred to protect those groups by utilizing suitable protecting groups, which are known in the art. The suitable protecting group can be described in the Protective Groups in Organic Synthesis by T. Greene.

The protecting group can be deprotected utilizing suitable deprotecting reagents such as those described in Protective Groups in Organic Synthesis by T. Greene.

Reaction Scheme 3

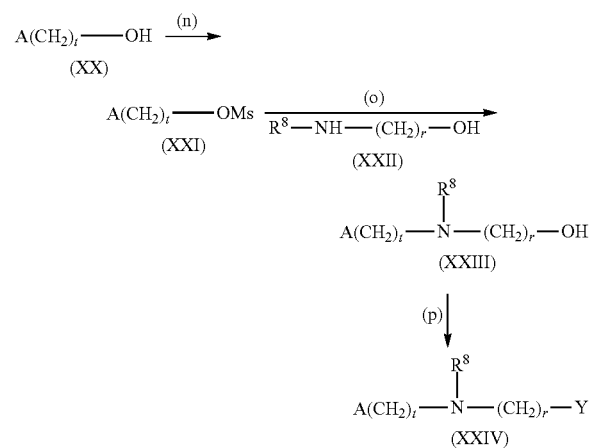

The compound of formula II where $R^6$ is hydrogen or halo or nitro, i.e. compounds of formula:

(II)

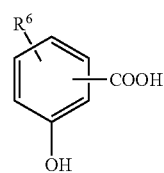

are either commercially available or can be prepared according to the methods described in the literature as follows:
1. 3-Br or $F\text{-}2\text{-}OHC_6H_3CO_2H$
Canadian Journal of Chemistry (2001), 79(11) 1541-1545.
2. $4\text{-}Br\text{-}2\text{-}OHC_6H_3CO_2H$
WO 9916747 or JP 04154773.
3. $2\text{-}Br\text{-}6\text{-}OHC_6H_3CO_2H$
JP 47039101.
4. $2\text{-}Br\text{-}3\text{-}OHC_6H_3CO_2H$
WO 9628423.

5. 4-Br-3-OHC$_6$H$_3$CO$_2$H
WO 2001002388.
6. 3-Br-5-OHC$_6$H$_3$CO$_2$H
Journal of labeled Compounds and Radiopharmaceuticals (1992), 31(3), 175-82.
7. 2-Br-5-OHC$_6$H$_3$CO$_2$H and 3-Cl-4-OHC$_6$H$_3$CO$_2$H
WO 9405153 and U.S. Pat. No. 5,519,133.
8. 2-Br-4-OHC$_6$H$_3$CO$_2$H and 3-Br-4-OHC$_6$H$_3$CO$_2$H
WO 20022018323
9. 2-Cl-6-OHC$_6$H$_3$CO$_2$H
JP 06293700
10. 2-Cl-3-OHC$_6$H$_3$CO$_2$H
Proceedings of the Indiana Academy of Science (1983), Volume date 1982, 92, 145-51.
11. 3-Cl-5-OHC$_6$H$_3$CO$_2$H
WO 2002000633 and WO 2002044145.
12. 2-Cl-5-OHC$_6$H$_3$CO$_2$H
WO 9745400.
13. 5-I-2-OHC$_6$H$_3$CO$_2$H and 3-I, 2-OHC$_6$H$_3$CO$_2$H
Z. Chem. (1976), 16(8), 319-320.
14. 4-I-2-OHC$_6$H$_3$CO$_2$H
Journal of Chemical Research, Synopses (1994), (11), 405.
15. 6-I-2-OHC$_6$H$_3$CO$_2$H
U.S. Pat. No. 4,932,999.
16. 2-I-3-OHC$_6$H$_3$CO$_2$H and 4-I-3-OHC$_6$H$_3$CO$_2$H
WO 9912928.
17. 5-I-3-OHC$_6$H$_3$CO$_2$H
J. Med. Chem. (1973), 16(6), 684-7.
18. 2-I-4-OHC$_6$H$_3$CO$_2$H
Collection of Czechoslovak Chemical Communications, (1991), 56(2), 459-77.
19. 3-I-4-OHC$_6$H$_3$CO$_2$,
J.O.C. (1990), 55(18), 5287-91.

The compound of formula II, where R$^6$ is alkoxy having from 1 to 3 carbon atoms, and in which the substituents are at the positions indicated in the following structure:

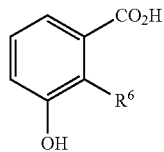

can be synthesized via the reaction of Scheme 4.

In the reaction of Scheme 4, R$^{10}$ is alkyl group having from 1 to 2 carbon atoms. P is a hydroxyl protecting group.

The compound of formula XXV can be converted to the compound of formula XXVI via reaction of step (q) by protecting phenol by suitable protecting group known to those skilled in the art. The suitable conditions for the protecting group can be described in the Protective Groups in Organic Synthesis by T. Greene.

The compound of formula XXVI can be converted to the compound of formula XXVII by oxidation of aldehyde to carboxylic acid. The reaction can be carried out by using suitable oxidizing reagents for example, pyridinium chlorochromate, potassium permanganate, sodium permanganate and the like. Any of the conditions suitable in such oxidation reactions can be utilized to carry out the reaction of step (r).

The compound of formula XXVII can be converted to the compound of formula XXVIII via reaction of step (s) where R$^6$ is alkoxy having 1 carbon atom by deprotection of protecting group. The suitable deprotecting conditions can be described in the Protective Groups in Organic Synthesis by T Greene.

The compound of formula XXVII can be converted to the compound of formula XXIX by treating the compound of formula XXVII with boron tribromide or boron trichloride using solvent for example dichloromethane for 4 to 48 hours at the temperature from −72° C. to 0° C. Any of the conditions conventional in such reactions can be utilized to carry out the reaction of step (t).

The compound of formula XXIX can be converted to the compound of formula XXX by esterification of the compound of formula XXIX with methanol or ethanol. The reaction can be carried out either by using catalysts for example H$_2$SO$_4$, TsOH and the like or by using dehydrating agent for example dicyclohexylcarbodiimide/DMAP and the like. Any of the conditions conventional in such esterification reactions can be utilized to carry out the reaction of step (u).

The compound of formula XXX can be converted to the compound of formula XXXI by etherifying or alkylating the compound of formula XXX with alkyl halide having 2 to 3 carbon atoms in the presence of suitable base for example potassium carbonate, cesium carbonate, sodium hydride, pyridine and the like. The reaction can be carried out in conventional solvents, such as tetrahydrofuran, N, N-dimethylformamide, dichloromethane and the like. The reaction is generally carried out at temperatures from 0° C. to 40° C. Any of the conditions suitable in such alkylation reactions can be utilized to carry out the reaction of step (v).

The compound of formula XXXI can be converted to the compound of formula XXXII via reaction of step (w) where R$^6$ is alkoxy having 2 to 3 carbon atoms by deprotection of protecting group. The suitable deprotecting conditions can be described in the Protective Groups in Organic Synthesis by T Greene.

The product can be isolated and purified by techniques such as extraction, evaporation, chromatography, and recrystallization.

Reaction Scheme 4

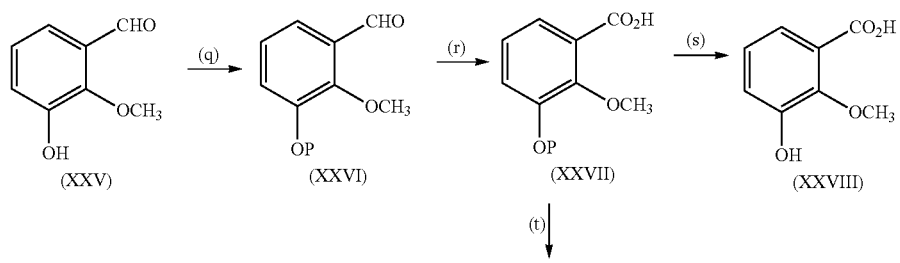

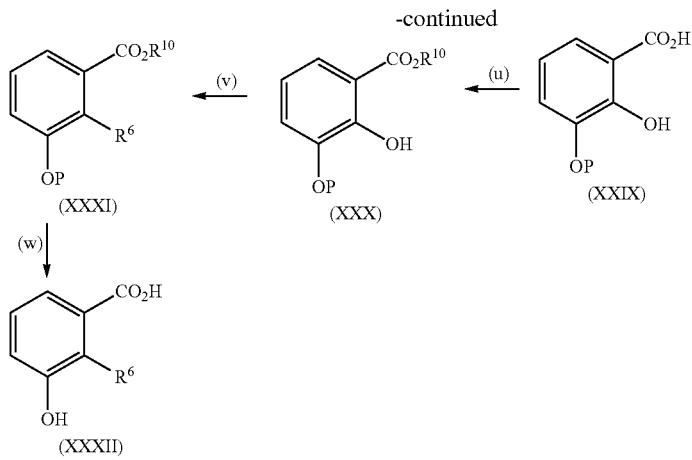

Compounds of formula II (other than those described above in connection with Reaction Scheme 4), where $R^6$ is alkoxy having from 1 to 3 carbon atoms, i.e. compounds of formula:

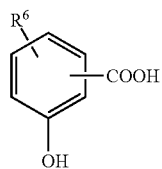

(II)

are either commercially available or can be prepared according to the methods described in the literature as follows:
1. 2-OMe-4-OHC$_6$H$_3$CO$_2$H
US 2001034343 or WO 9725992.
2. 5-OMe-3-OHC$_6$H$_3$CO$_2$H
J.O.C. (2001), 66(23), 7883-88.
3. 2-OMe-5-OHC$_6$H$_3$CO$_2$H
U.S. Pat. No. 6,194,406 (Page 96) and Journal of the American Chemical Society (1985), 107(8), 2571-3.
4. 3-OEt-5-OHC$_6$H$_3$CO$_2$H
Taiwan Kexue (1996), 49(1), 51-56.
5. 4-OEt-3-OHC$_6$H$_3$CO$_2$H
WO9626176
6. 2-OEt-4-OHC$_6$H$_3$CO$_2$H
Takeda Kenkyusho Nempo (1965), 24,221-8.
JP 07070025.
7. 3-OEt-4-OHC$_6$H$_3$CO$_2$H
WO9626176.
8. 3-OPr-2-OHC$_6$H$_3$CO$_2$H
JP 07206658, DE 2749518.
9. 4-OPr-2-OHC$_6$H$_3$CO$_2$H
Farmacia (Bucharest) (1970), 18(8), 461-6.
JP 08119959.
10. 2-OPr-5-OHC$_6$H$_3$CO$_2$H and 2-OEt-5-OHC$_6$H$_3$CO$_2$H
Adapt synthesis from U.S. Pat. No. 6,194,406 (Page 96) by using propyl iodide and ethyl iodide.
11. 4-OPr-3-OHC$_6$H$_3$CO$_2$H
Adapt synthesis from WO 9626176
12. 2-OPr-4-OHC$_6$H$_3$CO$_2$H
Adapt synthesis from Takeda Kenkyusho Nempo (1965), 24,221-8 by using propyl halide.
13. 4-OEt-3-OHC$_6$H$_3$CO$_2$H
Biomedical Mass Spectrometry (1985), 12(4), 163-9.
14. 3-OPr-5-OHC$_6$H$_3$CO$_2$H
Adapt synthesis from Taiwan Kexue (1996), 49(1), 51-56 by using propyl halide.

The compound of formula II, where $R^6$ is an alkyl having from 1 to 3 carbon atoms, i.e. compounds of formula:

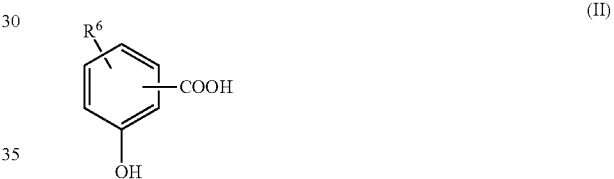

(II)

are either commercially available or can be prepared according to the methods described in the literature as follows:
1. 5-Me-3-OHC$_6$H$_3$CO$_2$H and 2-Me-5-OHC$_6$H$_3$CO$_2$H
WO 9619437.
J.O.C. 2001, 66, 7883-88.
2. 2-Me-4-OHC$_6$H$_3$CO$_2$H
WO 8503701.
3. 3-Et-2-OHC$_6$H$_3$CO$_2$H and 5-Et-2-OHC$_6$H$_3$CO$_2$H
J. Med. Chem. (1971), 14(3), 265.
4. 4-Et-2-OHC$_6$H$_3$CO$_2$H
Yaoxue Xuebao (1998), 33(1), 67-71.
5. 2-Et-6-OHC$_6$H$_3$CO$_2$H and 2-n-Pr-6-OHC$_6$H$_3$CO$_2$H
J. Chem. Soc., Perkin Trans 1 (1979), (8), 2069-78.
6. 2-Et-3-OHC$_6$H$_3$CO$_2$H
JP 10087489 and WO 9628423.
7. 4-Et-3-OHC$_6$H$_3$CO$_2$H
J.O.C. 2001, 66, 7883-88.
WO 9504046.
8. 2-Et-5-OHC$_6$H$_3$CO$_2$H
J.A.C.S (1974), 96(7), 2121-9.
9. 2-Et-4-OHC$_6$H$_3$CO$_2$H and 3-Et-4-OHC$_6$H$_3$CO$_2$H
JP 04282345.
10. 3-n-Pr-2-OHC$_6$H$_3$CO$_2$H
J.O.C. (1991), 56(14), 4525-29.
11. 4-n-Pr-2-OHC$_6$H$_3$CO$_2$H
EP 279630.
12. 5-n-Pr-2-OHC$_6$H$_3$CO$_2$H
J. Med. Chem. (1981), 24(10), 1245-49.
13. 2-n-Pr-3-OHC$_6$H$_3$CO$_2$H
WO 9509843 and WO 9628423.

14. 4-n-Pr-3-OHC$_6$H$_3$CO$_2$H
WO 9504046.
15. 2-n-Pr-5-OHC$_6$H$_3$CO$_2$H
Synthesis can be adapted from J.A.C.S (1974), 96(7), 2121-9 by using ethyl alpha formylvalerate.
16. 3-n-Pr-4-OHC$_6$H$_3$CO$_2$H
Polymer (1991), 32(11) 2096-105.
17. 2-n-Pr-4-OHC$_6$H$_3$CO$_2$H
3-Propylphenol can be methylated to 3-Propylanisole, which was then formylated to 4-Methoxy-3-benzaldehyde. The aldehyde can be oxidized by Jone's reagent to give corresponding acid and deprotection of methyl group by BBr$_3$ will give the title compound.
18. 1. 3-Et-5-OHC$_6$H$_3$CO$_2$H and 3-Pr-n-5-OHC$_6$H$_3$CO$_2$H
Adapt synthesis from J.O.C. 2001, 66, 7883-88 by using 2-Ethylacrolein and 2-Propylacrolein.

The compound of formula II, where R$^6$ is cyano, i.e. compounds of formula:

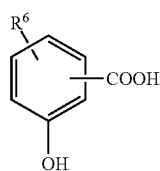
(II)

can be synthesized via the reaction of Scheme 5.

In the reaction of scheme 5, A, X, q, t, and r are described as above. R$^7$ is alkyl group having from 1 to 3 carbon atoms. P$_1$ is hydroxy protecting group.

The compound of formula XXXIII can be converted to the compound of formula XXXIV via reaction of step (x) by protecting phenol by suitable protecting group known to those skilled in the art. The suitable conditions for the protecting group can be described in the Protective Groups in Organic Synthesis by T. Greene.

The compound of formula XXXIV can be reduced to the compound of formula XXXV via reaction of step (y) by utilizing metals for example Zn, Sn, or Fe and acid, or by catalytic hydrogenation. Any conventional conditions in such reductions can be utilized to carry out the reaction of step (y).

The compound of formula XXXV can be converted to the compound of formula XXXVI via reaction of step (z) by various methods known to those skilled in the art for example, diazotization of amine using aqueous sulfuric acid at higher temperatures and then by adding aqueous sodium nitrite at 0-5° C. The intermediate aryl diazonium salt can be converted to the compound of formula XXXVI either via Sandmeyer reaction using Cu(I) cyanide in DMF at high temperature or diazonium salt is further heated with aqueous sulfuric acid at 100-110° C. to give the hydroxy which can be converted to triflate. Palladium catalyzed displacement of the triflate with cyanide for example zinc cyanide in DMF can be utilized to give compound of formula XXXVI. Any conventional conditions in such conversion of amine to nitrile can be utilized to carry out the reaction of step (z).

The compound of formula XXXVI can be converted to the compound of formula XXXVII via reaction of step (a') by deprotection of hydroxy protecting group. The suitable deprotecting conditions can be described in the Protective Groups in Organic Synthesis by T Greene.

The compound of formula XXXVII can be converted to the compound of XXXVIII via reaction of step (b') in the same manner as described hereinbefore in connection with the reaction of step (b).

The compound of formula XXXVIII is the compound of formula II where R$^6$ is cyano and R$^7$ is alkyl group having from 1 to 3 carbon atoms.

The compound of formula XXXVIII can be converted to the compound of formula II where R$^7$ is H by ester hydrolysis. Any conventional conditions in ester hydrolysis will produce the compound of formula II where R$^7$ is H and R$^6$ is cyano.

The product of each step can be isolated and purified by techniques such as extraction, evaporation, chromatography, and recrystallization.

If A is substituted by hydroxy or amino groups, it is generally preferred to protect those groups by utilizing suitable protecting groups, which are known in the art. The suitable protecting group can be described in the Protective Groups in Organic Synthesis by T. Greene.

The protecting group can be deprotected utilizing suitable deprotecting reagents such as those described in Protective Groups in Organic Synthesis by T. Greene.

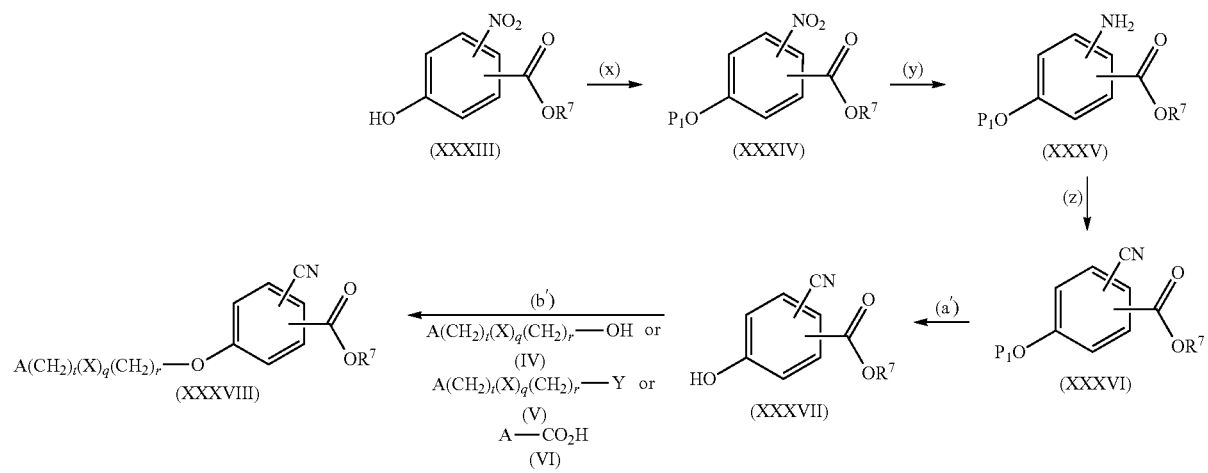

Reaction Scheme 5

The compound of formula II, where $R^6$ is hydroxy, i.e. compounds of formula:

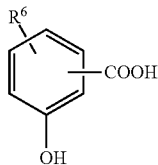

(II)

can be synthesized via the reaction of Scheme 6.

In the reaction of scheme 6, A, X, q, t, and r are described as above. $R^7$ is alkyl group having from 1 to 3 carbon atoms. $P_1$ and $P_2$ are hydroxyl protecting groups.

The compound of formula XXXV can be converted to the compound of formula XXXIX via reaction of step (c') by diazotization of amine using aqueous sulfuric acid at higher temperatures and then by addition of aqueous sodium nitrite at 0-5° C. The intermediate aryl diazonium salt can be further heated with aqueous sulfuric acid at 100-110° C. to give the compound of formula XXXIX.

In the compound of formula XXXIX, hydroxy can be protected by suitable protecting group known to those skilled in the art to give the compound of formula XL via reaction of step (d'). The suitable conditions for the protecting group can be described in the Protective Groups in Organic Synthesis by T. Greene.

The compound of formula XL can be converted to the compound of formula XLI via reaction of step (e') by deprotection of selective hydroxy protecting group. The suitable deprotecting conditions can be described in the Protective Groups in Organic Synthesis by T Greene.

The compound of formula XLI can be converted to the compound of formula XLII via reaction of step (f') in the same manner as described hereinbefore in connection with the reaction of step (b).

The compound of formula XLII can be converted to the compound of formula XLIII via reaction of step (g') by deprotection of hydroxy protecting group. The suitable deprotecting conditions can be described in the Protective Groups in Organic Synthesis by T Greene.

The compound of formula XLIII is the compound of formula II where $R^6$ is hydroxy and $R^7$ is alkyl group having from 1 to 3 carbon atoms.

The compound of formula XLIII can be converted to the compound of formula II where $R^7$ is H by ester hydrolysis. Any conventional conditions in ester hydrolysis will produce the compound of formula II where $R^7$ is H and $R^6$ is hydroxy.

The product of each step can be isolated and purified by techniques such as extraction, evaporation, chromatography, and recrystallization.

If A is substituted by hydroxy or amino groups, it is generally preferred to protect those groups by utilizing suitable protecting groups, which are known in the art. The suitable protecting group can be described in the Protective Groups in Organic Synthesis by T. Greene.

The protecting group can be deprotected utilizing suitable deprotecting reagents such as those described in Protective Groups in Organic Synthesis by T. Greene.

Reaction Scheme 6

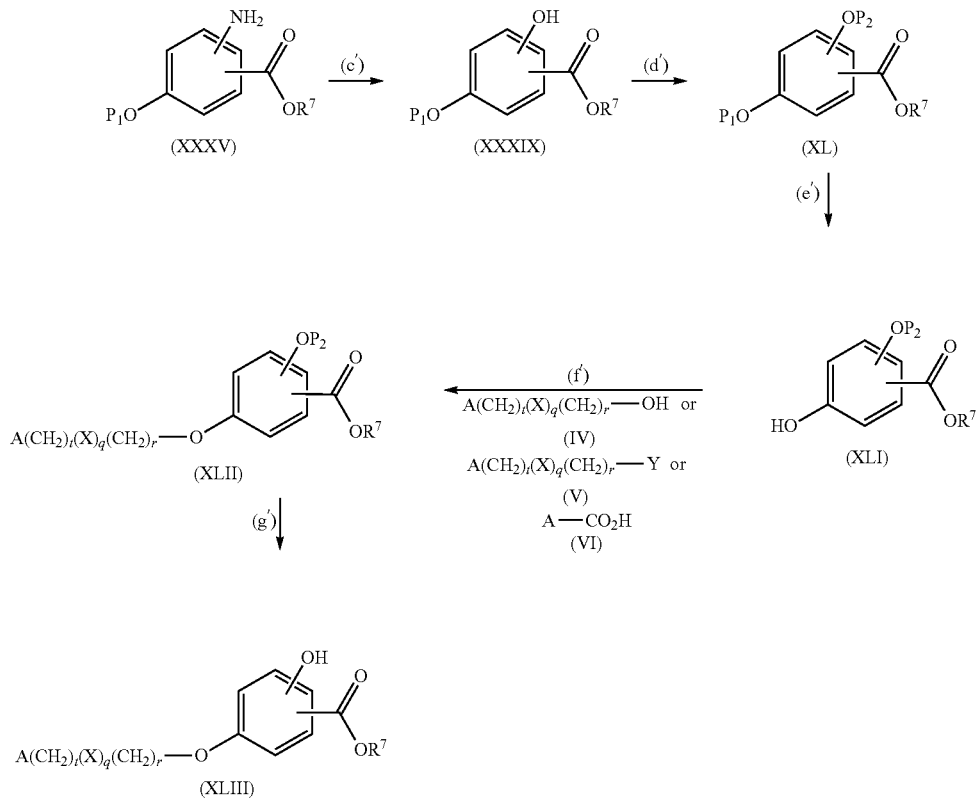

The compound of formula II, where $R^6$ is thio or alkylthio, i.e. compounds of formula:

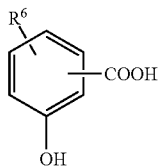

(II)

can be synthesized via the reaction of Scheme 7.

In the reaction of scheme 7, A, X, q, t, and r are described as above. $R^7$ and $R^{11}$ are alkyl groups having from 1 to 3 carbon atoms. $P_1$ is hydroxy protecting group.

The compound of formula XXXV can be converted to the compound of formula XLIV via reaction of step (h') by diazotization of amine using aqueous sulfuric acid at higher temperatures and then by adding aqueous sodium nitrite solution at 0-5° C. The intermediate aryl diazonium salt can be converted to the compound of formula XLIV by various methods known to those skilled in the art for example, utilizing Sandmeyer-type reaction of aryl diazonium salt with copper(I) salts such as copper(I) chloride, copper (I) bromide or using catalytic amount of copper salt with KI, KBr and the like. Any of the conditions conventional in such reactions can be utilized to carry the reaction of step (h').

The compound of formula XLIV can be converted to the compound of formula XLVI via reaction of step (i') by coupling the compound of formula XLIV with the compound of formula XLV utilizing palladium catalyst with ligands such as josiphos, DiPPF or Dppe. Any of the conditions conventional in such reactions can be utilized to carry the reaction of step (i').

The compound of formula XLVI can be converted to the compound of formula XLVIII via reaction of step (j') where $R^6$ is alkylthio by deprotection of hydroxy protecting group. The suitable deprotecting conditions can be described in the Protective Groups in Organic Synthesis by T Greene.

The compound of formula XLVIII can be converted to the compound of formula XLIX where $R^6$ is alkylthio via reaction of step (n') in the same manner as described hereinbefore in connection with the reaction of step (b).

The compound of formula XLIX is the compound of formula II where $R^6$ is alkylthio and $R^7$ is alkyl group having from 1 to 3 carbon atoms.

The compound of formula XLIX can be converted to the compound of formula L where $R^7$ is H by ester hydrolysis.

Any conventional conditions in ester hydrolysis will produce the compound of formula II where $R^7$ is H and $R^6$ is alkylthio.

The compound of formula XXXV can be converted to the compound of formula XXXIX via reaction of step (k') in the same manner as described hereinbefore with the connection with the reaction of step (c').

The compound of formula XXXIX can be converted to the compound of formula XLVII via reaction of step (l') by reaction of the compound of formula XXXIX with thioacetic acid in the presence TPP and diisopropylamine. Any of the conditions conventional in such reactions can be utilized to carry the reaction of step (l').

The compound of formula XLVII can be converted to the compound of formula XLVIII where $R^6$ is thio via reaction of step (m') by deprotection of hydroxy protecting group. The suitable deprotecting conditions can be described in the Protective Groups in Organic Synthesis by T Greene.

The compound of formula XLVIII can be converted to the compound of formula XLIX where $R^6$ is thio via reaction of step (n') in the same manner as described hereinbefore in connection with the reaction of step (b).

The compound of formula XLIX can be converted to the compound of formula L via reaction of step (o') by hydrolysis of compound of formula XLIX with sodium or potassium hydroxide. Any of the conditions conventional in such hydrolysis reactions can be utilized to carry the reaction of step (o').

The compound of formula L is the compound of formula II where $R^6$ is thio and $R^7$ is H.

The compound of formula L can be converted to the compound of formula II by esterification of the compound of formula L with $R^7OH$. The reaction can be carried out either by using catalyst for example $H_2SO_4$, TsOH or by using dehydrating agent for example dicyclohexylcarbodiimide and the like. Any of the conditions conventional in such esterification reactions can be utilized to carry out the reaction to give compound of formula II where $R^7$ is alkyl having from 1 to 3 carbon atoms and $R^6$ is thio.

The product of each step can be isolated and purified by techniques such as extraction, evaporation, chromatography, and recrystallization.

If A is substituted by hydroxy or amino groups, it is generally preferred to protect those groups by utilizing suitable protecting groups, which are known in the art. The suitable protecting group can be described in the Protective Groups in Organic Synthesis by T. Greene.

The protecting group can be deprotected utilizing suitable deprotecting reagents such as those described in Protective Groups in Organic Synthesis by T. Greene.

Reaction Scheme 7

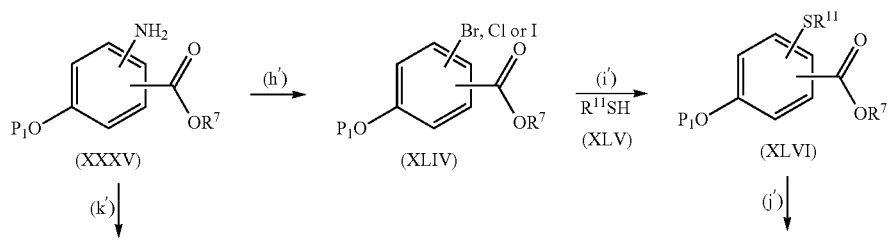

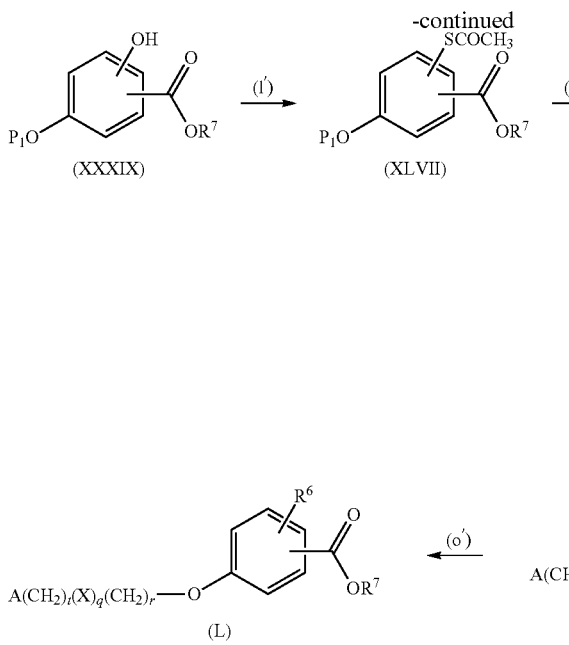
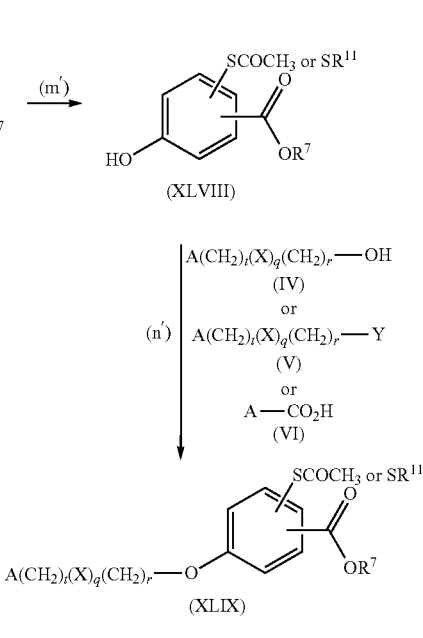

Uses and Methods of Treatment

This invention provides a method for reducing uric acid levels in a mammalian subject or increasing uric acid excretion from a mammalian subject. The level of uric acid in a mammal can be determined using any conventional measure. Typically the level of uric acid in the blood is determined. Uric acid can also be deposited or precipitated in tissues, resulting in depots (e.g. tophi) that can be affected by raising or lowering blood uric acid concentrations, and which conversely can contribute to circulating uric acid. The method of this invention for reducing uric acid can be used to treat or prevent a variety of conditions including gout, hyperuricemia, elevated levels of uric acid that do not meet the levels customarily justifying a diagnosis of hyperuricemia, kidney stones, renal dysfunction, cardiovascular disease, cardiovascular risk factor, and cognitive impairment. By lowering uric acid levels, administration of the compounds of this invention slows progression of kidney disease. An elevated uric acid level has been identified as a risk factor for cardiovascular disease. A significant correlation has been shown between elevated uric acid and cognitive impairment in older adults. (Schretlen, D. J. et al., "Serum Uric Acid and Cognitive Function in Community-Dwelling Older Adults", Neuropsychology (January 2007) 21(1): 136-140). Accordingly, the method of this invention for reducing uric acid can be used to treat or prevent cognitive impairment, including cognitive impairment in elderly adults. It is well known that people with Lesch-Nyhan Syndrome have elevated levels of uric acid and suffer the numerous consequences of this hyperuricemia, including gout. Thus, this invention for reducing blood levels and increasing elimination of uric acid can be used to treat people with Lesch-Nyhan Syndrome.

The normal range of uric acid in blood is between 3.4 mg/dL and 7.0 mg/dL in men, between 2.4 mg/dL and 6.0 mg/dL in premenopausal women, and from 2.5 mg/dL to 5.5 mg/dL in children. Urate crystal formation/precipitation typically occurs in men at levels of 6.6 mg/dL or higher and in women at levels of 6.0 mg/dL or higher. This illustrates that levels of uric acid that are within the so-called normal range can have undesirable health consequences, even producing gout. Also, what may be in the normal range for the population as a whole may be elevated for the individual. Cardiovascular and other consequences of elevated uric acid can occur with blood levels well within these "normal" ranges. Therefore, a diagnosis of hyperuricemia is not necessarily a prerequisite for the beneficial effects of the compounds of the invention.

This invention includes the treatment of hyperuricemia associated with gout, hypertension, vascular inflammation, heart failure, arterio-venous disorders, myocardial infarct, stroke, pre-eclampsia, eclampsia, sleep apnea, renal dysfunction (including renal failure, end stage renal disease [ESRD]), organ transplant, diuretics, thiazides, cyclosporine, aspirin, vitamin C, nicotinic acid, levodopa (L-DOPA), cytotosic drugs, and certain antibacterial agents (such as pyrozinamide), cirrhosis, thyroid dysfunction, parathyroid dysfunction, lung cancer, anemia, leukemia, lymphoma, multiple myeloma, tumor-lysis syndrome, thyroid or parathyroid dysfunction, Lesch-Nyhan Syndrome, smoking, alcohol consumption, and psoriasis. This invention includes the treatment of hyperuricemia that can lead to gout, formation of urate crystals, renal dysfunction, graft or organ failure following transplant, endothelial disorders (such as inflammation), chronic heart failure, arterio-venous disorders, pre-eclampsia, eclampsia, hypertension, and cognitive impairment. In embodiments of the method of this invention for treating gout, tissue deposits of uric acid, including but not limited to tophi, are reduced, and the incidence and severity of gout flares are also reduced. In an embodiment of this invention, the subject undergoing uric acid-lowering treatment does not have diabetes, insulin resistance syndrome, or metabolic syndrome.

The compounds of this invention can be administered by any conventional route of systemic administration. Preferably they are administered orally. Accordingly, it is preferred for the medicament to be formulated for oral administration. Other routes of administration that can be used in accordance with this invention include rectally, parenterally, by injection (e.g. intravenous, subcutaneous, intramuscular or intraperitoneal injection), or nasally.

Further embodiments of each of the uses and methods of treatment of this invention comprise administering any one of the embodiments of the compounds described above. In the interest of avoiding unnecessary redundancy, each such compound and group of compounds is not being repeated, but they are incorporated into this description of uses and methods of treatment as if they were repeated.

Both human and non-human mammalian subjects can be treated in accordance with the treatment method of this invention. The optimal dose of a particular compound of the invention for a particular subject can be determined in the clinical setting by a skilled clinician. In the case of oral administration the compound of this invention is generally administered to adults in a daily dose of from 1 mg to 2500 mg, more preferably from 1 mg to 1200 mg. In other embodiments of this invention the compound is administered in a dose of from 400 mg to 1000 mg, from 600 mg to 800 mg, from 600 mg to 1000 mg, or from 100 to 300 mg, administered once or twice per day. The average body weight of a typical adult is 60 to 70 kilograms, so that appropriate dose ranges expressed as mg/kg are approximately from 0.015 to 42 mg/kg, from 0.015 to 20 mg/kg, from 6.6 to 13 mg/kg, from 10 to 13 mg/kg, from 10 to 16 mg/kg, or from 1.67 to 4.3 mg/kg, administered once or twice per day. When treating children the optimal dose is determined by the patient's physician. In the case of oral administration to a mouse the compound of this invention is generally administered in a daily dose from 1 to 300 mg of the compound per kilogram of body weight.

The compound of this invention can be administered in combination with other uric acid lowering drugs. In such cases the dose of the compound of this invention is as described above. Any conventional or investigational uric acid lowering drug can be utilized in combination with the compound of this invention. Examples of such drugs include xanthine oxidase inhibitors such as allopurinol (from 100 mg/day to 1000 mg/day; more typically from 100 mg/day to 300 mg/day) febuxostat (from 40 mg/day to 120 mg/day; more specifically from 60 mg/day to 80 mg/day) and oxypurinol; Puricase/PEG-uricase (from 4 mg to 12 mg every two weeks by infusion); uricosuric agents such as sulfinpyrazone (from 100 mg/day to 800 mg/day), probenecid (500 mg/day), losartan (from 25 mg/day to 200 mg/day, more typically from 50 mg/day to 100 mg/day), fenofibrate, JTT-552 (a URAT-1 inhibitor), benzbromarone (from 70 mg/day to 150 mg/day), and statins such as atorvastatin (LIPITOR®). The other uric acid lowering drug can be administered in its usual amount or in an amount that is less than the usual amount, whether by administering lower doses of such other drug or by less frequent dosing with such other drug.

The compounds of this invention can be administered together with other drugs used to decrease the pain associated with gouty attacks, for example nonsteroidal antiinflammatory drugs (NSAIDs), colchicine, corticosteroids, and other analgesics.

In the course of lowering uric acid levels in the blood it is expected that the compounds of this invention will increase the levels of uric acid in the urine. To increase the pH of the urine and thereby improve solubility of the uric acid, citrate or bicarbonate, for example, can be administered in conjunction with the compound of this invention.

An admixture of the compound or salt of this invention with one or more other uric acid lowering drugs, analgesics, and pH increasing agents, can be administered to the subject. Alternatively the compound or salt of this invention and the one or more other uric acid lowering drugs, analgesics, and pH increasing agents are not mixed together to form an admixture but are administered independently to the subject. When the active ingredients are not mixed together to form a single admixture or composition it is convenient to provide them in the form of a kit comprising one or more unit oral doses of a compound of this invention, one or more unit oral doses of one or more other uric acid lowering drugs, analgesics, and pH increasing agents, and instructions for administering the compound of this invention in combination with the other active ingredients. Preferably the components of the kit are packaged together, such as in a box or a blister pack.

Pharmaceutical Compositions

This invention provides a pharmaceutical composition comprising a compound of this invention, and optionally a pharmaceutically acceptable carrier. Further embodiments of the pharmaceutical composition of this invention comprise any one of the embodiments of the compounds described above. In the interest of avoiding unnecessary redundancy, each such compound and group of compounds is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 1 mg to 2500 mg, more preferably from 1 mg to 1200 mg of the compound of this invention. In more specific embodiments of this invention the oral composition will comprise from 400 mg to 1000 mg, from 600 mg to 800 mg, from 600 mg to 1000 mg, or from 100 to 300 mg, of the compound of this invention. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The active ingredients can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants.

The invention will be better understood by reference to the following examples, which illustrate but do not limit the invention described herein.

EXAMPLES

Example 1

3-(2,6-dimethylbenzyloxy)-4-methylbenzoic acid

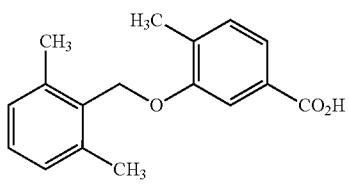

Step A: Preparation of Ethyl 3-(2,6-dimethylbenzyloxy)-4-methylbenzoate

To a stirred solution of Ethyl 3-hydroxy-4-methylbenzoate (7.81 g, 43.3 mmol), and $K_2CO_3$ (11.97 g, 86.7 mmol) in dry DMF (30 ml) was added 2,6-Dimethylbenzyl chloride (7.37 g, 47.6 mmol) at room temperature under argon. The reaction mixture was stirred for 16 hours at the room temperature, diluted with ethyl acetate and washed with water (2×), and brine. The organic layer was dried over $Na_2SO_4$, filtered, concentrated, and purified by flash chromatography on a silica gel column (hexane:ethyl acetate, 2:1) to give the title compound as white solid.
$^1$H NMR (400 MHz, CDCl$_3$): 1.31 (t, 3H); 2.11 (s, 3H); 2.33 (s, 6H); 4.31 (q, 2H); 5.10 (s, 2H); 7.0-7.2 (m, 3H); 7.3 (d, 1H); 7.5 (d, 1H); 7.63 (s, 1H).

Step B: Preparation of 3-(2,6-dimethylbenzyloxy)-4-methylbenzoic acid

To a stirred solution of Ethyl 3-(2,6-dimethylbenzyloxy)-4-methylbenzoate (Step A, 7.96 g, 26.6 mmol) in absolute ethanol (120 ml) was added 1N NaOH (60 ml) at room temperature. The reaction mixture was stirred for 4 hours, or until all the starting material is consumed, acidified to pH 3.5-4.0 by adding 1N HCl and concentrated. The residue was taken into chloroform and washed with 0.1N HCl, brine, dried over $Na_2SO_4$, filtered, concentrated and purified by flash chromatography on a silica gel column (chloroform:methanol, 95:5 spiked with acetic acid) to give the title compound as white solid.
$^1$H NMR (400 MHz, d-DMSO): 2.10 (s, 3H); 2.33 (s, 6H); 5.08 (s, 2H); 7.07 (d, 2H); 7.1 (t, 1H); 7.25 (d, 1H); 7.5 (d, 1H); 7.7 (s, 1H).

Step A: Preparation of Ethyl 3-hydroxy-4-nitrobenzoate

To a stirred solution of 3-hydroxy-4-nitrobenzoic acid (10 g, 54.6 mmol) in ethanol (100 ml) was added p-TsOH (1.03 g, 5.4 mmol) at room temperature under argon and the reaction mixture was refluxed for 12 hours or until all the starting material is consumed. The reaction mixture was concentrated, diluted with ethyl acetate and washed with 0.1N HCl, brine, dried over $Na_2SO_4$, filtered, concentrated and purified by flash chromatography on a silica gel column (chloroform:methanol, 95:5) to give the title compound as solid.
$^1$H NMR (400 MHz, CDCl$_3$): 1.41 (t, 3H); 4.40 (q, 2H); 7.60 (d, 1H); 7.63 (s, 1H); 8.16 (d, 1H); 10.5 (s, 1H).

Step B: Preparation of Ethyl 3-(2,6-dimethylbenzyloxy)-4-nitrobenzoate

To a stirred solution of Ethyl 3-hydroxy-4-nitrobenzoate (Step A, 5.98 g, 28.3 mmol), and $K_2CO_3$ (7.83 g, 56.7 mmol) in dry DMF (25 ml) was added 2,6-Dimethylbenzyl chloride (4.38 g, 28.3 mmol) at room temperature under argon. The reaction mixture was stirred for 16 hours at the room temperature or until all the starting material is consumed, diluted with ethyl acetate, washed with water (2×), and brine. The organic layer was dried over $Na_2SO_4$, filtered, concentrated, and purified by flash chromatography on a silica gel column (hexane:ethyl acetate, 4:1) to give the title compound as light yellow solid.
$^1$H NMR (400 MHz, CDCl$_3$): 1.43 (t, 3H); 2.41 (s, 6H); 4.43 (q, 2H); 5.25 (s, 2H); 7.0-7.2 (m, 3H); 7.72 (d, 1H); 7.77 (d, 1H); 7.92 (s, 1H).

Step C: Preparation of 3-(2,6-dimethylbenzyloxy)-4-nitrobenzoic acid

To a stirred solution of Ethyl 3-(2,6-dimethylbenzyloxy)-4-nitrobenzoate (Step B, 5.97 g, 18.1 mmol) in absolute ethanol (75 ml) was added 1N NaOH (40 ml) at room temperature. The reaction mixture was stirred for 4 hours, or until starting material is consumed, acidified to pH 3.5-4.0 by adding 1N HCl and concentrated. The residue was taken into chloroform and washed with 0.1N HCl, brine, dried over $Na_2SO_4$, filtered, concentrated and purified by flash chromatography on a silica gel column (chloroform:methanol, 95:5 spiked with acetic acid) to give the title compound as yellow solid.
$^1$H NMR (400 MHz, d-DMSO): 2.32 (s, 6H); 5.30 (s, 2H); 7.05 (d, 2H); 7.07 (m, 1H); 7.77 (d, 1H); 7.94 (d, 1H); 8.0 (s, 1H).

Example 2

3-(2,6-dimethylbenzyloxy)-4-nitrobenzoic acid

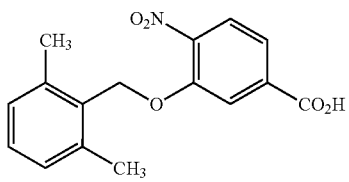 [SMILES: Cc1cccc(C)c1COc1cc(C(=O)O)ccc1[N+](=O)[O-]]

Example 3

3-(2,6-dimethylbenzyloxy)-4-methoxybenzoic acid

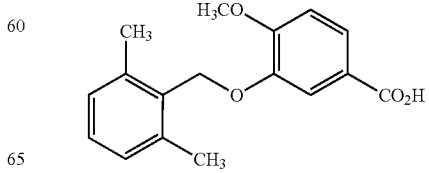

Step A: Preparation of Ethyl 3-hydroxy-4-methoxybenzoate

To a stirred solution of 3-hydroxy-4-methoxybenzoic acid (10 g, 59.4 mmol) in ethanol (100 ml) was added p-TsOH (2.26 g, 11.9 mmol) at room temperature under argon and the reaction mixture was refluxed for 16 hours or until all the starting material is consumed. The reaction mixture was concentrated, diluted in ethyl acetate and washed with 0.1N HCl, brine, dried over $Na_2SO_4$, filtered, concentrated and purified by flash chromatography on a silica gel column (hexane:ethyl acetate, 2:1) to give the title compound as white solid.

$^1$H NMR (400 MHz, $CDCl_3$): 1.37 (t, 3H); 3.94 (s, 3H); 4.32 (q, 2H); 6.85 (d, 1H); 7.59-7.62 (m, 2H).

Step B: Preparation of Ethyl 3-(2,6-dimethylbenzyloxy)-4-methoxybenzoate

To a stirred solution of Ethyl 3-hydroxy-4-methoxybenzoate (Step A, 3.24 g, 16.5 mmol), and $K_2CO_3$ (4.56 g, 33 mmol) in dry DMF (20 ml) was added 2,6-Dimethylbenzyl chloride (2.55 g, 16.5 mmol) at room temperature under argon. The reaction mixture was stirred for 16 hours at the room temperature or until all the starting material is consumed, diluted with ethyl acetate, washed with water (2×), and brine. The organic layer was dried over $Na_2SO_4$, filtered, concentrated, and purified by flash chromatography on a silica gel column (hexane:ethyl acetate, 4:1) to give the title compound as white solid.

$^1$H NMR (400 MHz, $CDCl_3$): 1.40 (t, 3H); 2.42 (s, 6H); 3.87 (s, 3H); 4.36 (q, 2H); 5.12 (s, 2H); 6.89-6.91 (m, 1H); 7.06-7.2 (m, 3H); 7.71-7.73 (m, 2H).

Step C: Preparation of 3-(2,6-dimethylbenzyloxy)-4-methoxybenzoic acid

To a stirred solution of Ethyl 3-(2,6-dimethylbenzyloxy)-4-methoxybenzoate (Step B, 5.52 g, 17.5 mmol) in absolute ethanol (100 ml) was added 1N NaOH (35 ml) at room temperature. The reaction mixture was stirred for 4 hours, or until starting material is consumed, acidified to pH 3.5-4.0 by adding 1N HCl and concentrated. The residue was taken into chloroform and washed with 0.1N HCl, brine, dried over $Na_2SO_4$, filtered, concentrated and purified by flash chromatography on a silica gel column (chloroform:methanol, 95:5 spiked with acetic acid) to give the title compound as white solid.

$^1$H NMR (400 MHz, $CDCl_3$): 2.42 (s, 6H); 3.89 (s, 3H); 5.13 (s, 2H); 6.93-6.95 (m, 1H); 7.05-7.2 (m, 3H); 7.77 (m, 2H).

Example 4

3-(2,6-dimethylbenzyloxy)-4-fluorobenzoic acid

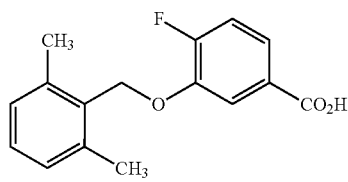 [SMILES: Cc1cccc(C)c1COc1cc(C(=O)O)ccc1F]

Step A: Preparation of Ethyl 4-fluoro-3-hydroxybenzoate

To a stirred solution of 4-fluoro-3-hydroxybenzoic acid (2 g, 12.8 mmol) in ethanol (100 ml) was added p-TsOH (0.487 g, 2.56 mmol) at room temperature under argon. The reaction mixture was refluxed for 16 hours or until all the starting material is consumed.

The reaction mixture was concentrated, diluted in ethyl acetate and washed with 0.1N HCl, brine, dried over $Na_2SO_4$, filtered, concentrated and purified by flash chromatography on a silica gel column (hexane:ethyl acetate, 2:1) to give the title compound as white solid.

$^1$H NMR (400 MHz, $CDCl_3$): 1.38 (t, 3H); 4.31 (q, 2H); 7.09-7.14 (m, 1H); 7.6 (m, 1H); 7.70-7.73 (d, 1H).

Step B: Preparation of Ethyl 3-(2,6-dimethylbenzyloxy)-4-fluorobenzoate

To a stirred solution of Ethyl 4-fluoro-3-hydroxybenzoate (Step A, 2.66 g, 14.4 mmol), and $K_2CO_3$ (3.99 g, 29 mmol) in dry DMF (20 ml) was added 2,6-Dimethylbenzyl chloride (2.44 g, 15.8 mmol) at room temperature under argon. The reaction mixture was stirred for 16 hours at room temperature or until all the starting material is consumed, diluted with ethyl acetate, washed with water (2×), and brine. The organic layer was dried over $Na_2SO_4$, filtered, concentrated, and purified by flash chromatography on a silica gel column (hexane:ethyl acetate, 4:1) to give the title compound as solid.

$^1$H NMR (400 MHz, $CDCl_3$): 1.41 (t, 3H); 2.42 (s, 6H); 4.36 (q, 2H); 5.16 (s, 2H); 7.09-7.1 (m, 4H); 7.7 (m, 1H); 7.8 (d, 1H).

Step C: Preparation of 3-(2,6-dimethylbenzyloxy)-4-fluorobenzoic acid

To a stirred solution of Ethyl 3-(2,6-dimethylbenzyloxy)-4-fluorobenzoate (Step B, 4.08 g, 13.5 mmol) in absolute ethanol (60 ml) was added 1N NaOH (30 ml) at room temperature. The reaction mixture was stirred for 4 hours, or until starting material is consumed, acidified to pH 3.5-4.0 by adding 1N HCl and concentrated. The residue was taken into chloroform and washed with 0.1N HCl, brine, dried over $Na_2SO_4$, filtered, concentrated and purified by flash chromatography on a silica gel column (chloroform:methanol, 95:5 spiked with acetic acid) to give the title compound as white solid.

$^1$H NMR (400 MHz, d-DMSO): 2.32 (s, 6H); 5.17 (s, 2H); 7.05 (m, 2H); 7.2 (m, 1H); 7.3 (m, 1H); 7.6 (m, 1H); 7.8 (d, 1H).

Comparative Example 5

4-amino-3-(2,6-dimethylbenzyloxy)benzoic acid

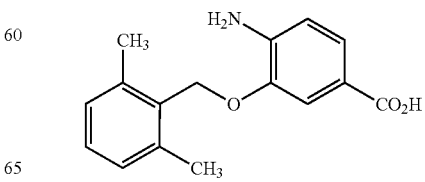

Step A: Preparation of 4-amino-3-(2,6-dimethylbenzyloxy)benzoic acid

To a stirred solution of 3-(2,6-dimethylbenzyloxy)-4-nitrobenzoic acid (1.06 g, 3.5 mmol) in ethanol (45 ml) was added $SnCl_4 \cdot 2H_2O$ (4 g, 17.5 mmol) and the reaction mixture was refluxed for 3 hours or until all the starting material is consumed. The reaction mixture was concentrated, diluted with chloroform, and washed with 2M NaOH to bring pH to 7. The organic layer was washed with brine, dried over $Na_2SO_4$, filtered, concentrated, and purified by flash chromatography on a silica gel column (chloroform:methanol, 9:1) to give the title compound as off white solid.

$^1H$ NMR (400 MHz, d-DMSO): 2.34 (s, 6H); 5.04 (s, 2H); 5.8 (s, 2H); 6.61 (d, 1H); 7.05 (d, 2H); 7.1 (m, 1H); 7.4 (d, 1H); 7.48 (s, 1H); 12.1 (s, 1H).

Biological Activity Example 6: URAT1 Inhibition Assay

URAT1 (Uric Acid Transporter 1) is expressed on the apical membrane in renal tubules. It mediates the re-uptake of uric acid from the urine into the blood. Inhibition of URAT1 leads to increased excretion of uric acid in the urine, and is therefore a potential mode of action for drugs that lower serum uric acid concentrations. Probenecid and Benzbromarone, for example, have been used clinically for treatment of gout and hyperuricemia, and they both act on URAT1 to reduce uric acid reuptake. However, benzbromarone was withdrawn from the market due to liver toxicity via mechanisms independent of URAT1, and probenecid acts on numerous transporter proteins, resulting in interactions with a variety of other drugs.

An in vitro URAT1 assay is useful for identifying compounds with potential activity in lowering serum uric acid. A suitable assay involves transfection of cells (e.g. human embryonic kidney cells; "HEK") with a vector encoding human URAT1, followed by determination of the ability of transfected cells to take up radiolabeled uric acid. The activity of compounds as URAT1 inhibitors is evaluated by their ability to block uric acid uptake by transfected cells.

Test Compounds and Chemicals:

Benzbromarone (Sigma, Cat.No.B5774), Probenecid (Sigma, Cat.No.P8761)), DMSO (Sigma, Cat.No.D-2650), [8-$^{14}$C] Urate (50-60 mCi/mmol; American Radio Chemicals, Cat. No. ARC0513).

Subcloning of hURAT1 into the Expression Vector:

Plasmid vector pCMV6-XL5 containing hURAT1 cDNA (Cat. No. SC125624) and the expression vector pCMV6-Neo (Cat. No.pCMVNEO) were obtained from OriGene Technologies, Inc. The full-length hURAT1 cDNA was obtained from the vector pCMV6-XL5 and subcloned into the expression vector pCMV6-Neo to create the hURAT1 expression plasmid pCMV6-hURAT1. The sequences were verified by automatic DNA sequencing.

Cell Culture, transfection of URAT1 expressing plasmids and the establishment of stably expressing HEK cells for hURAT1:

Human embryonic kidney 293 (HEK) cells (ATTCC, Cat No. CRL-1573) were cultured in EMEM supplemented with 10% FBS and 2 mM L-glutamine and incubated at 37° C. and 5% $CO_2$. For transfection experiments, cells were plated on 60 mm dishes in 1 ml media per dish. After an 18-24 hour incubation, cells were transfected with plasmid pCMV6-hURAT1 or the expression vector pCMV6-Neo, using the Lipofectin trasfection agent following the manufacturer's instructions (Invitrogen, Cat.No. 18292). After transfection cells were grown in EMEM media for 72 hours and then by adding 1mg/ml Geneticin (GIBCO, Cat. No 10131) stable transfectants were selected. Stable transfectants expressing hURAT1 (herein after referred as hURAT1-HEK cells) or cells having only the expression vector pCMV6-Neo (herein after referred as mock-HEK cells) were verified using reverse transcription polymerase chain reaction (RT-PCR) methods.

[8-$^{14}$C] Urate Uptake Assay:

hURAT1-HEK cells and mock-HEK cells were plated in poly-D-Lysine Cell culture 24 well plates (Becton Dickinson, Cat. No. 354414) at a concentration of $3 \times 10^5$ in EMEM medium and incubated overnight. Reaction solutions containing the [8-$^{14}$C] urate (55 mCi/mmol) at a final concentration of 50 μM were prepared with or without test compounds in Hanks' balanced salt solution (HBSS) containing 125 mM sodium gluconate, 4.8 mM potassium gluconate, 1.3 mM calcium, 5.6 mM glucose, 1.2 mM magnesium sulfate, 1.2 mM $KH_2PO_4$ and 25 mM HEPES (pH7.4). Before the uptake assay started, the culture medium was removed and the cells were incubated for 5 min in 0.6 ml of HBSS. After that HBSS was removed, the prepared reaction solutions were added into each well and incubated for 5 min at room temperature. Then the reaction solution was removed, cells were washed twice with 0.6 ml of cold HBSS and lysed with 0.2 ml of 0.1 M NaOH for 20 min. The cell lysates were transferred into the scintillation vials containing 1 ml of scintillation fluid (Opti Phase SuperMIX, PerkinElmer, Cat No. 1200-439) and the radioactivity was counted in the Microbeta counter (1450, Wallac Jet, PerkinElmer). Test compounds were dissolved in DMSO and the same concentration of DMSO was added into the wells of mock-HEK cells and the hURAT1-HEK cells that didn't contain test compounds. For each test compound, the uptake assay was performed 2 times and carried out in triplicate. Urate uptake of the cells for each test condition was presented as the average percent inhibition in comparison to the DMSO control. The radioactivity values obtained for the wells that contained DMSO were taken as 100% uptake of the cells. The observed concentration-percent inhibition data were fitted to a sigmoidal concentration-effect model, where:

$$\% \text{ Inhibition} = (100 * Conc^{Slope})/(IC50^{Slope} + Conc^{Slope})$$

$IC_{50}$ and slope estimates with their 95% confidence limits were determined by a non-linear, least-squares regression analysis using the Data Analysis Toolbox™ (MDL Information Systems, San Leandro, Calif., USA).

For assessment of activity of compounds as URAT1 inhibitors, the percent inhibition of uric acid uptake was typically assessed at a drug concentration of 10 micromolar (Table 1). Additional drug concentrations of one of the compounds were tested for determination of the IC-50 value (Table 2).

TABLE 1

Inhibitory effects of the test compounds at the concentration of 10 μM on $^{14}$C urate uptake in hURAT1-HEK cells

| Compound | % of inhibition (at 10 μM) | Standard Deviation |
| --- | --- | --- |
| FA | 83.2 | 2.20 |
| FB | 81.0 | 0.27 |
| FC | 89.2 | 0.37 |
| FD | 68.1 | 0.09 |

TABLE 1-continued

Inhibitory effects of the test compounds at the concentration of 10 μM on $^{14}$C urate uptake in hURAT1-HEK cells

| Compound | % of inhibition (at 10 μM) | Standard Deviation |
|---|---|---|
| FE | 10.0 | 5.79 |
| EH | 95.6 | 0.88 |

TABLE 2

| Compound FC | % of inhibition | |
|---|---|---|
| Concentration (μM) | Avg. | St. dev. |
| 100 | 97.779342 | 0.3522719 |
| 10 | 93.257878 | 0.2288688 |
| 1 | 49.821135 | 3.9805112 |
| 0.5 | 34.619595 | 4.4494808 |
| 0.1 | −1.0770975 | 5.561229 |
| 0.05 | 7.0763938 | 3.7192347 |

What is claimed is:

1. A method of reducing the uric acid concentration in blood of, or increasing uric acid excretion from, a mammalian subject having a condition selected from the group consisting of gout, hyperuricemia, elevated levels of uric acid that do not meet the levels customarily justifying a diagnosis of hyperuricemia, tumor-lysis syndrome, and *Plasmodium falciparum*-induced inflammation, comprising administering to the subject a compound represented by Formula IA or a pharmaceutically acceptable salt thereof, in an amount effective to reduce the uric acid concentration in blood of, or increase uric acid excretion from, the subject

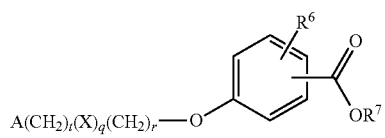

(IA)

wherein t is 0 or 1;

q is 0;

r is 0, 1 or 2;

$R^7$ is hydrogen or alkyl having from 1 to 3 carbon atoms;

$R^6$ is hydrogen, hydroxy, halo, alkyl having from 1 to 3 carbon atoms, alkoxy having from 1 to 3 carbon atoms, nitro, thio, alkylthio, or cyano;

A is phenyl, unsubstituted or substituted by 1 or 2 groups selected from halo, hydroxy, methyl, ethyl, perfluoromethyl, methoxy, ethoxy, perfluoromethoxy, nitro, and amino.

2. The method of claim 1, wherein A is 2,6-dimethylphenyl.

3. The method of claim 1, wherein the compound is represented by Formula IA1

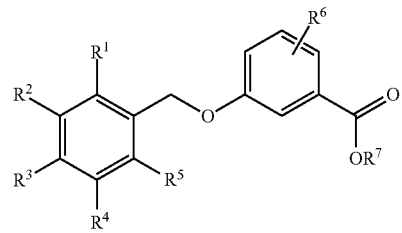

(IA1)

wherein two of $R^1$, $R^2$, $R^3$, $R^4$ and $R^5$ are selected from the group consisting of hydrogen, halo, hydroxy, methyl, ethyl, perfluoromethyl, methoxy, ethoxy and perfluoromethoxy, the remainder are hydrogen;

$R^7$ is hydrogen or alkyl having from 1 to 3 carbon atoms; and $R^6$ is hydrogen, halo, alkyl having from 1 to 3 carbon atoms, alkoxy having from 1 to 3 carbon atoms, or nitro.

4. The method of claim 3, wherein the compound is represented by Formula IA1a

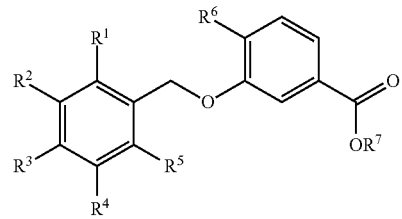

(IA1a)

and the variables are as defined in claim 3.

5. The method of claim 4, wherein $R^1$ is methyl and $R^5$ is methyl.

6. A method of reducing the uric acid concentration in blood of, or increasing uric acid excretion from, a mammalian subject having a condition selected from the group consisting of gout, hyperuricemia, elevated levels of uric acid that do not meet the levels customarily justifying a diagnosis of hyperuricemia, tumor-lysis syndrome, and *Plasmodium falciparum*-induced inflammation, comprising administering to the subject a compound selected from the group consisting of:

3-(2,6-dimethylbenzyloxy)-4-methylbenzoic acid;
3-(2,6-dimethylbenzyloxy)-4-nitrobenzoic acid;
3-(2,6-dimethylbenzyloxy)-4-methoxybenzoic acid;
3-(2,6-dimethylbenzyloxy)-4-fluorobenzoic acid;
and a pharmaceutically acceptable salt thereof,
in an amount effective to reduce the uric acid concentration in blood of, or increase uric acid excretion from, the subject.

7. The method of claim 1, wherein the subject is a human.

8. The method of claim 1, further comprising administering to the subject one or more other uric acid lowering drugs in a combined amount effective to reduce the uric acid concentration in blood of, or increase uric acid excretion from, the subject.

9. The method of claim 8, wherein the other uric acid lowering drug is selected from the group consisting of a xanthine oxidase inhibitor, a uricosuric agent, a urate transporter-1 inhibitor, a uricase, and a statin.

10. The method of claim 1, wherein the compound is formulated for oral administration.

* * * * *